United States Patent [19]

Hukuba

[11] 4,212,105
[45] Jul. 15, 1980

[54] INSPECTION DEVICE FOR CAVITIES

[76] Inventor: Hiroshi Hukuba, No. 914-1, Nazukari, Nagareyama-shi, Chiba-ken, Japan

[21] Appl. No.: 848,616

[22] Filed: Nov. 4, 1977

[30] Foreign Application Priority Data

| Nov. 10, 1976 [JP] | Japan | 51-135644 |
| Jun. 6, 1977 [JP] | Japan | 52-66511 |
| Jul. 12, 1977 [JP] | Japan | 52-83168 |
| Sep. 21, 1977 [JP] | Japan | 52-113829 |

[51] Int. Cl.² ............................................. A61C 3/00
[52] U.S. Cl. ...................................... 433/30; 350/305
[58] Field of Search ................... 32/69; 350/305, 235; 128/10, 11, 22

[56] References Cited

U.S. PATENT DOCUMENTS

| 1,342,351 | 6/1920 | Roy | 350/305 |
| 1,423,225 | 7/1922 | Knight | 32/69 |
| 1,509,041 | 9/1924 | Hyams | 32/69 |
| 2,107,791 | 2/1938 | Henning | 128/11 |
| 2,275,304 | 3/1942 | Maurud | 350/305 |

Primary Examiner—Robert Peshock
Attorney, Agent, or Firm—Blanchard, Flynn, Thiel, Boutell & Tanis

[57] ABSTRACT

An inspection device for cavities comprises a body and an inspection mirror which is installed on said body and is designed to be rotatable as well as tiltable in relation thereto.

36 Claims, 46 Drawing Figures

FIG. 5
FIG. 6
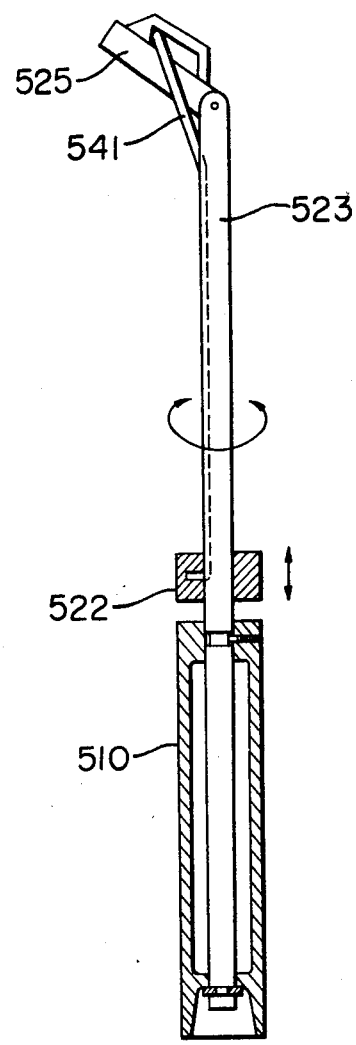
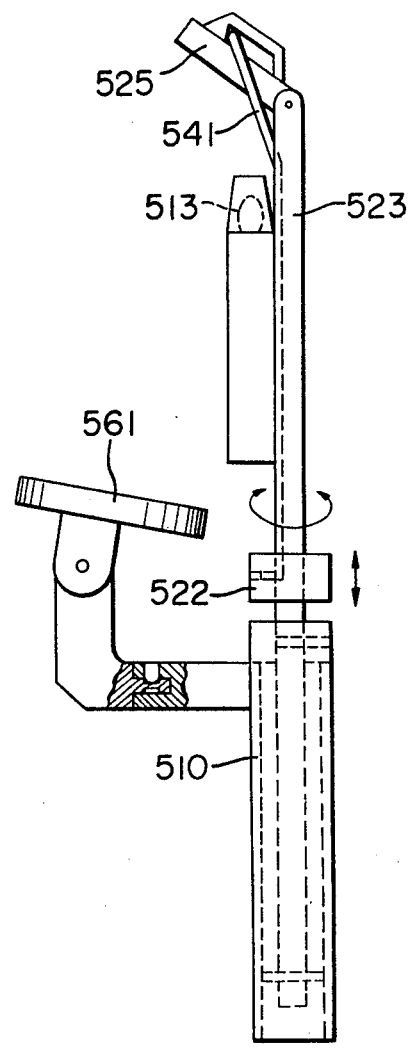

FIG. 8
FIG. 9
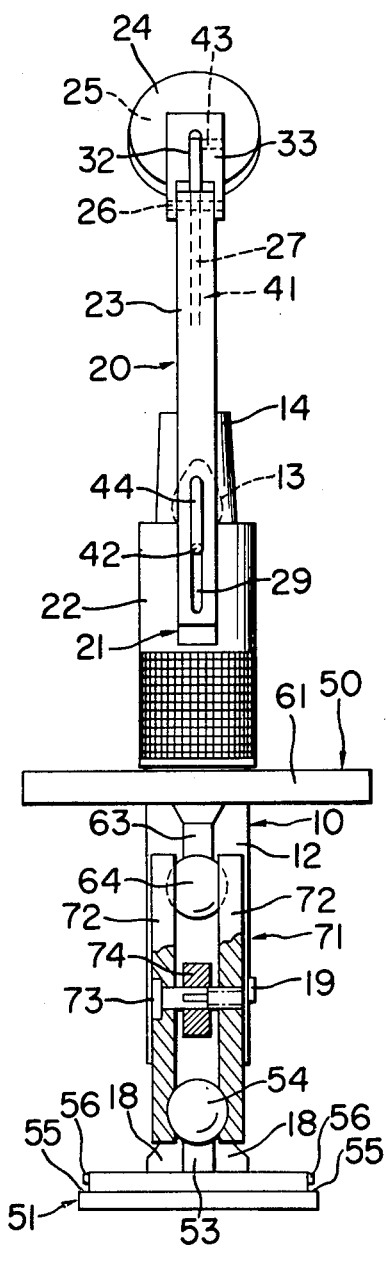
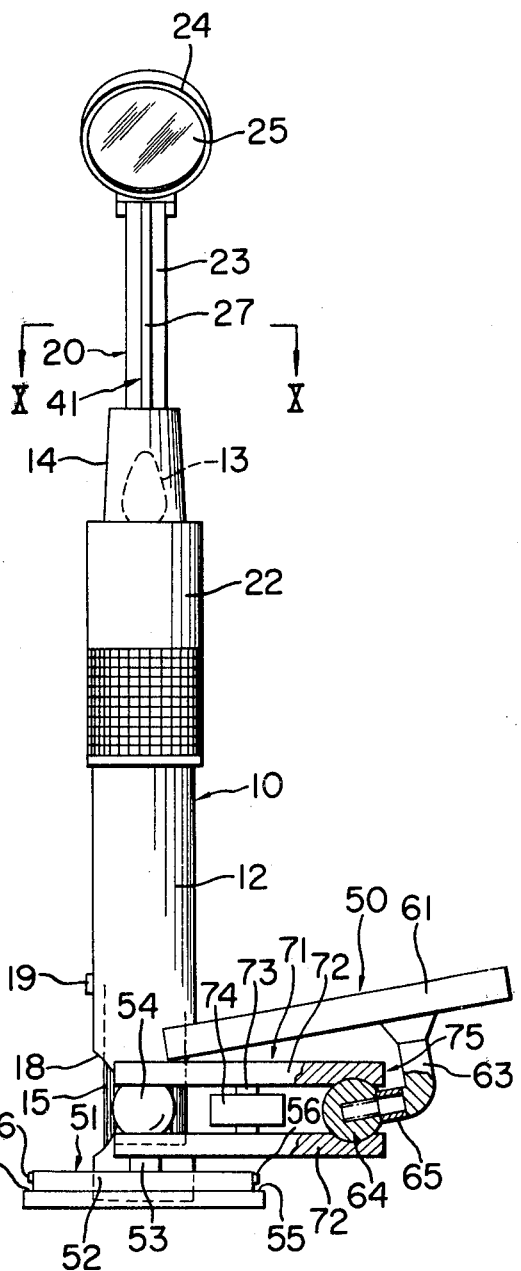

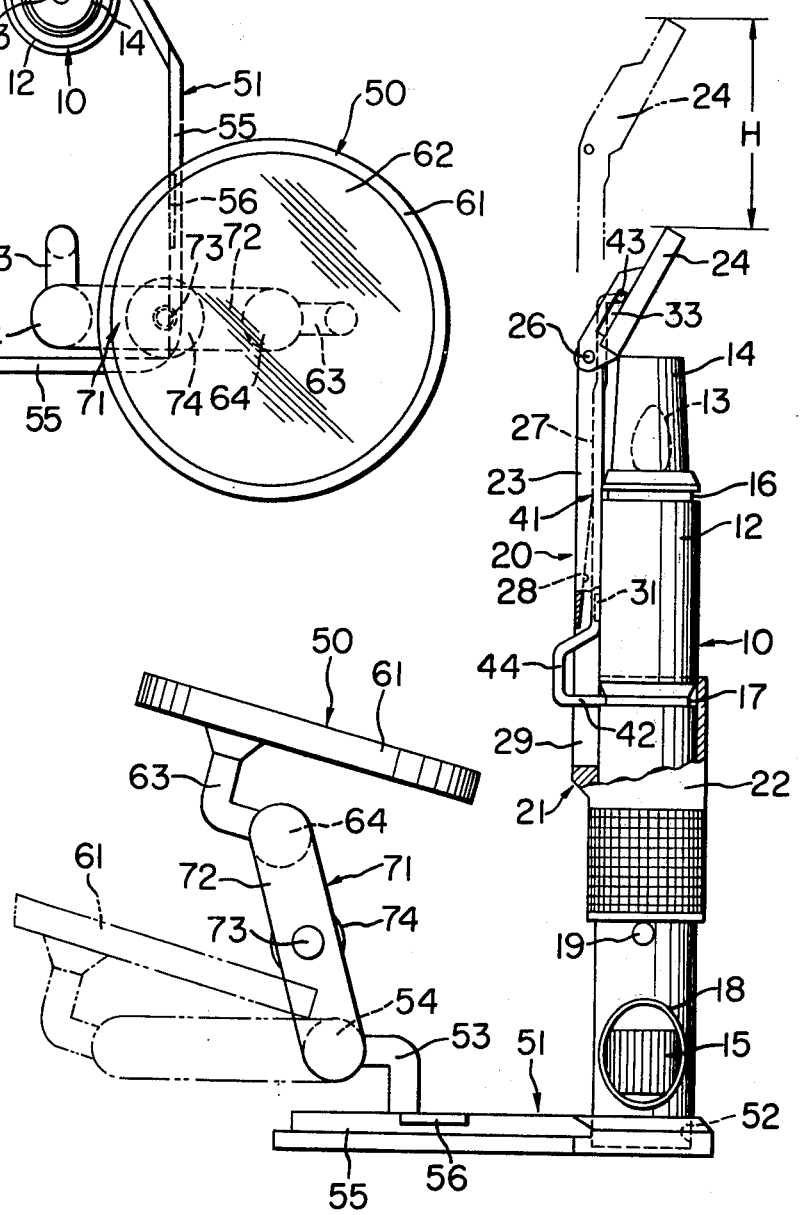

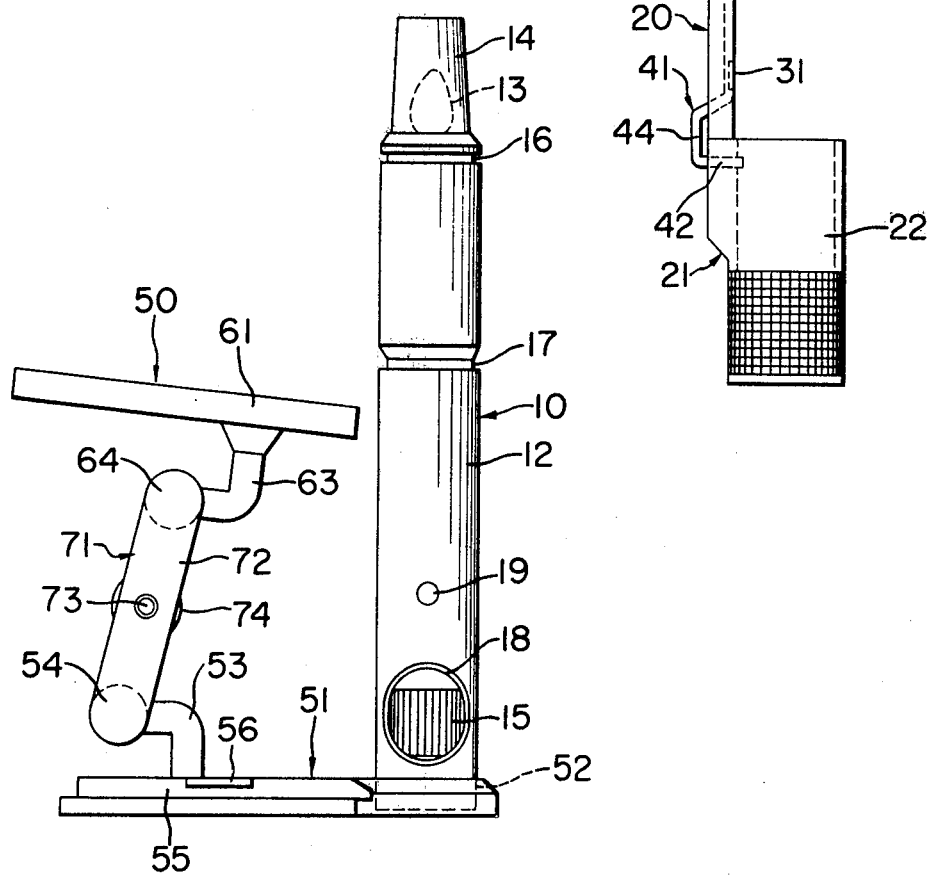

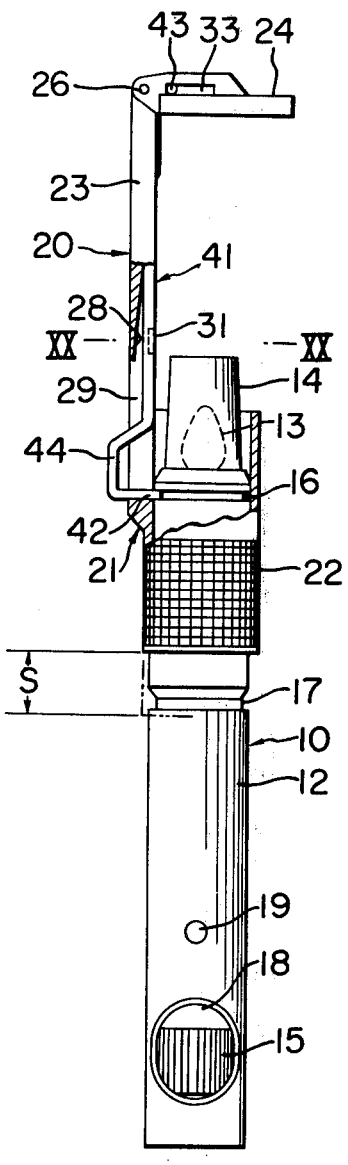
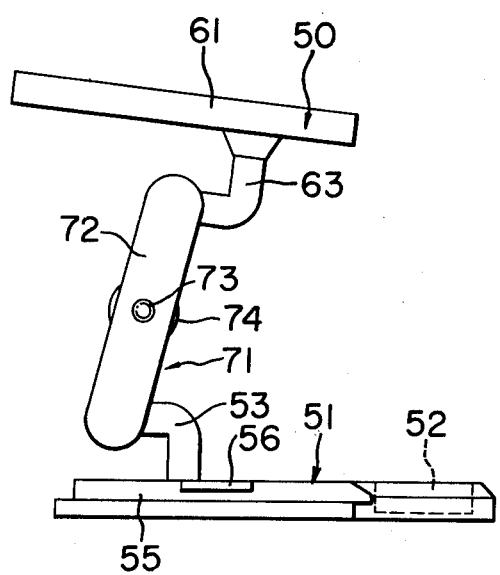
FIG. 14
FIG. 15

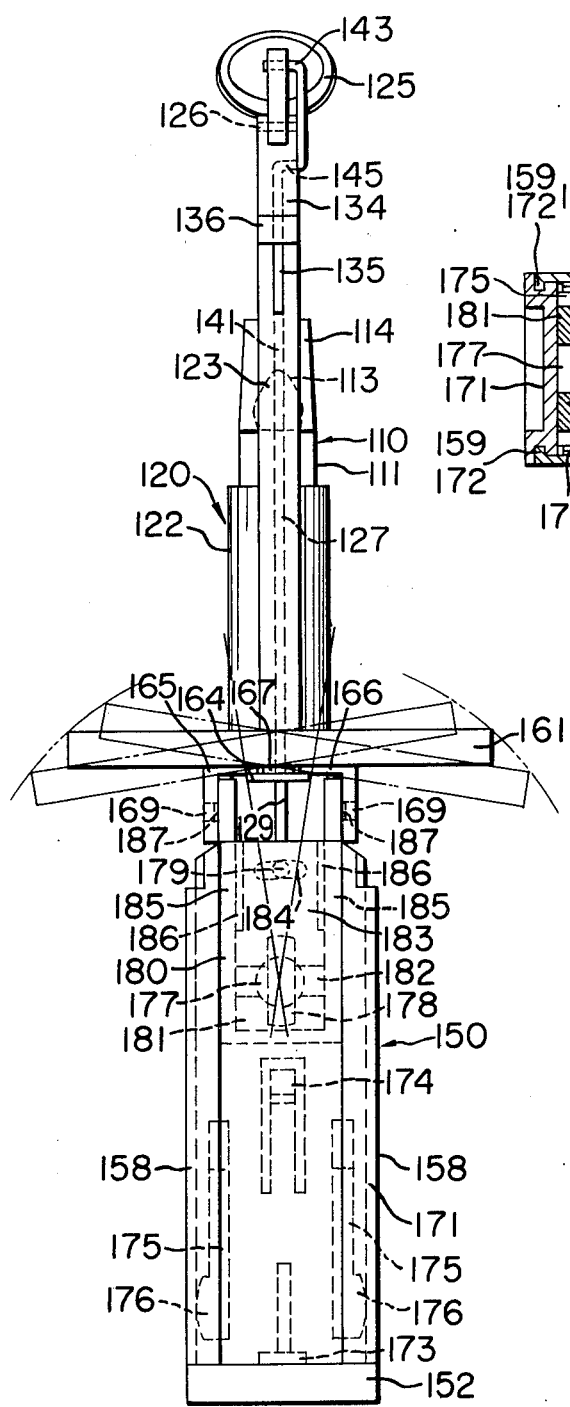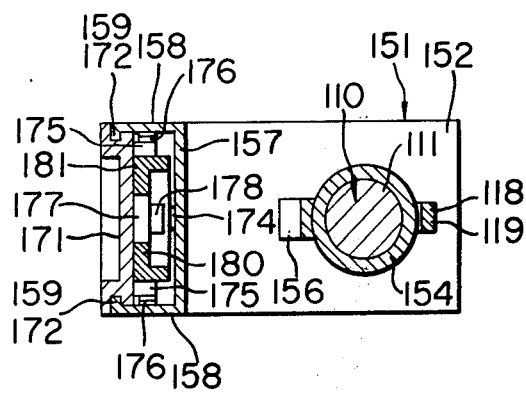

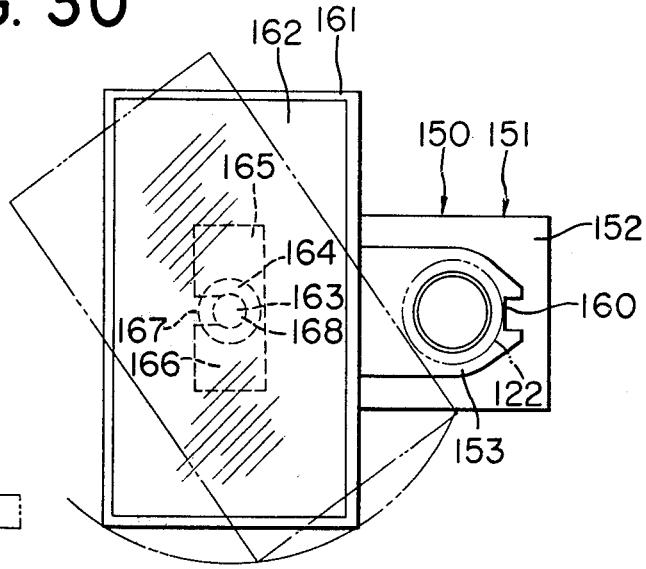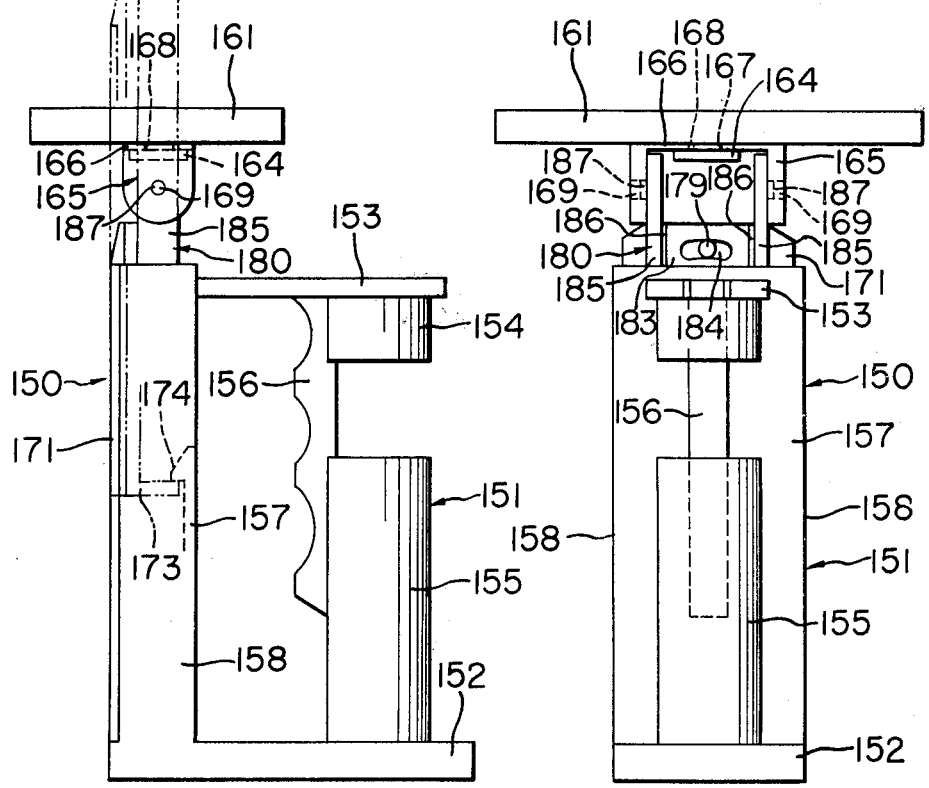

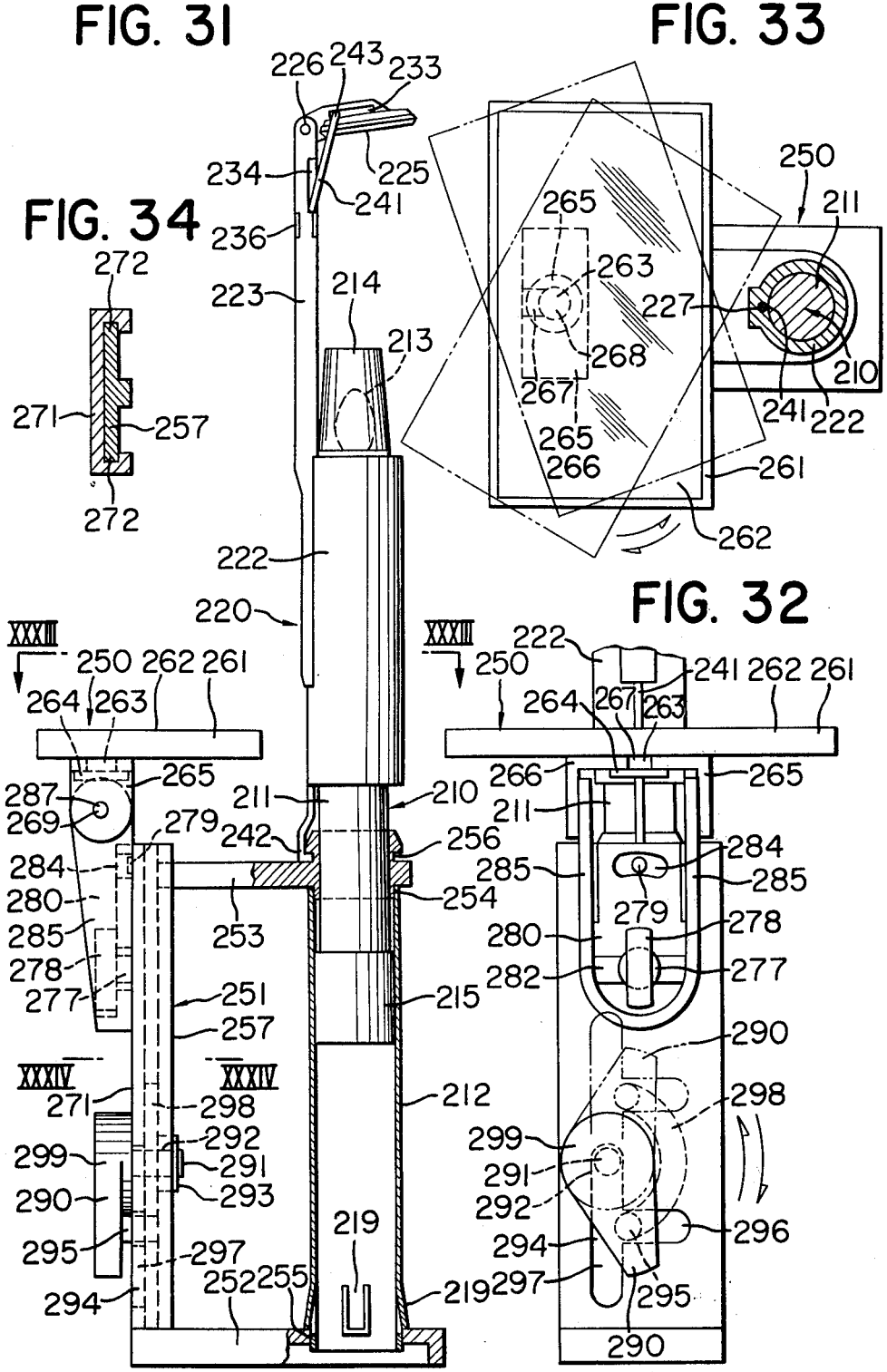

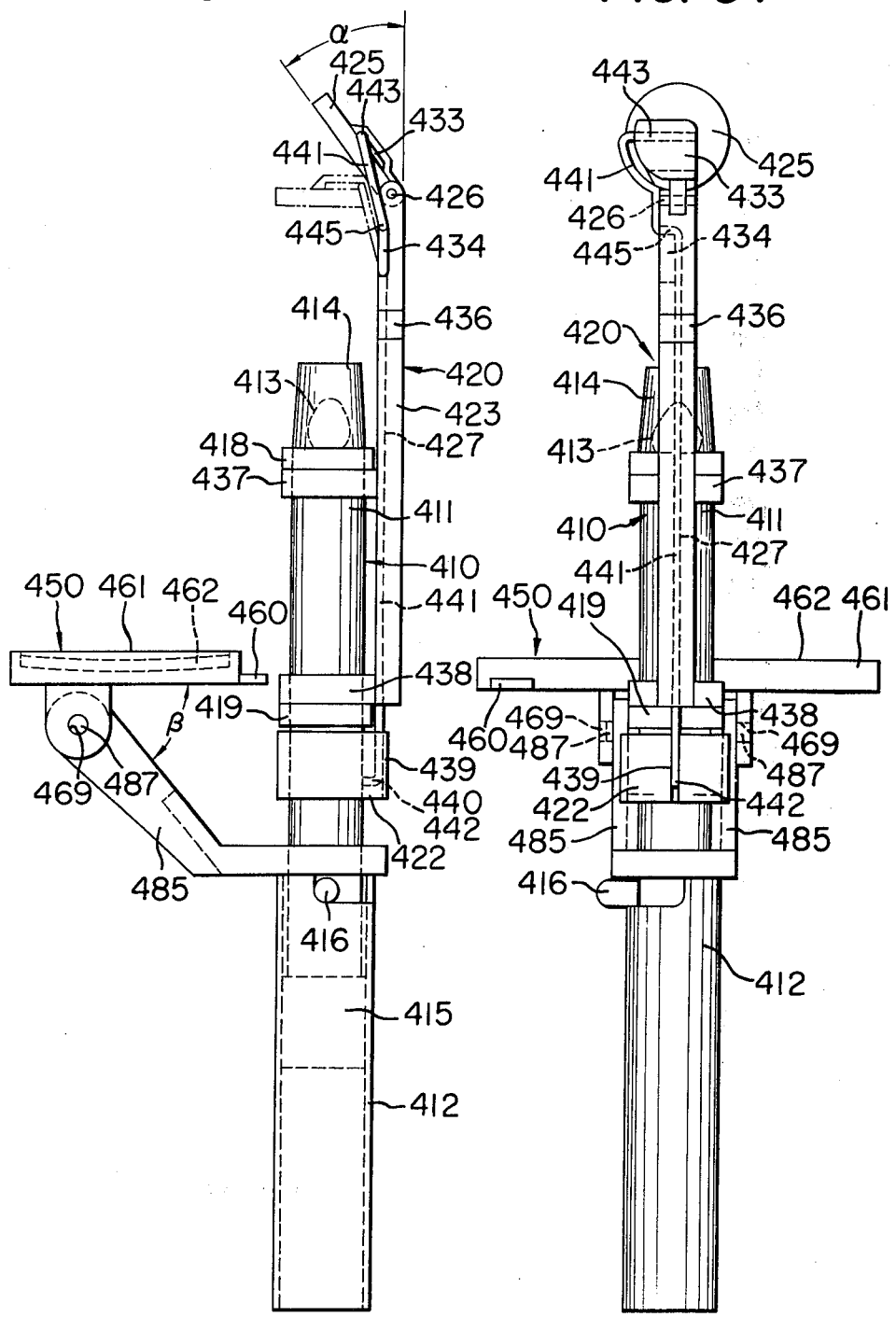

INSPECTION DEVICE FOR CAVITIES

BACKGROUND OF THE INVENTION

The present invention relates to an inspection device useful for self-inspection of cavities in the human body, particularly cavities in the mouth.

Inspection of cavities in the mouth, for instance, a cavity in a tooth, has hitherto been entrusted to dentists. However, it is desirable that one shall be able to take care of and manage one's own teeth daily. And yet, when one tries to inspect one's own teeth, because there is scarcely available any apposite instrument, one is obliged to resort to a small mirror with a handle such as for dental use, together with a hand mirror, while directing light on the tooth to be inspected. The state of things at the time of thus conducting the inspection of teeth is as illustrated in FIGS. 1 through 4.

In the case of inspecting the inner side of the left lower back teeth 1, as shown by a solid line in FIG. 2, the hand-mirror 6 is either held by the left hand 4 or placed on a desk, the handle 8 of the dental mirror 7 with a commercial pencil-light 9 fastened thereto is held by the right hand 5 and is inclined to the right at an angle of about A/2 in relation to a virtual line passing through the center of the mouth so as to make the image of the inner side of said left lower back teeth be thrown back by the dental mirror 7 to be reflexed in the center of the hand-mirror 6. The side view of the state of things on this occasion is as illustrated in FIG. 1. To be precise, the relative positions of the dental mirror 7 and the hand-mirror 6 are adjusted so that the projected light from the left lower back teeth 1 should repeat reflection optically and enter the eye.

In the case of inspecting the inner side of the right lower back-teeth 2, as shown by a double-dotted line in FIG. 2, the handle 8 of the dental mirror 7 is supposed to be inclined to the left at an angle of about A/2 in relation to said virtual line passing through the center of the mouth to perform the inspection.

On this occasion, if the right hand 5 is directly moved to the left, it would be in the way of the hand-mirror 6. Therefore, the handle 8 must be shifted from the right hand 5 to the left hand 4, or if the right hand 5 is continued to be used, the manner of holding the handle must be somehow changed.

The state of things at the time of inspecting the back side of the fore teeth is illustrated in FIGS. 3 and 4. As illustrated in FIG. 4, the handle 8 is inclined at an angle of about C/2 in relation to the virtual line passing through the center of the mouth and the dental mirror 7 is positioned in the back side of the lower fore-teeth 3. FIG. 3 is a side view of this occasion, and as illustrated therein, the dental mirror 7 must be erected practically parallel to the fore-teeth and, accordingly, the handle 8 is supposed to be moved through an angle of about B in the vertical direction compared with the case of inspecting the back-teeth illustrated in FIG. 1.

It will be understood from the foregoing description that inspection of the teeth by the use of the conventional dental mirror 7 is very troublesome as the position of the handle 8 of said dental mirror must be widely changed the horizontal as well as the vertical direction in front of the mouth by shifting said handle from the right hand to the left or from the left hand to the right, or changing the way of holding the mirror as often as the occasion demands, even when holding the mirror by the right hand. Such inconveniences are experienced not only in inspecting the inner parts of the lower teeth as stated above but also in inspecting other parts of the teeth.

SUMMARY OF THE INVENTION

A primary object of the present invention is to provide an inspection device for cavities, which eliminates the drawbacks of the conventional devices as described above.

Another object of the present invention is to provide an inspection device for cavities, wherein a body is equipped with an inspection mirror which is rotatably as well as tiltably mounted in relation thereto, thereby making easier the operation of said device as well as the inspection movements.

A further object of the present invention is to provide an inspection device for cavities, which includes an illumination means in addition to said body and inspection mirror, whereby it is possible to inspect a part to be inspected under bright illumination.

A still further object of the present invention is to provide an inspection device for cavities, wherein the body is equipped with an ocular mirror which is designed to cooperate with said inspection mirror, to wit, the object mirror, thereby making it possible to inspect a part through said object mirror and said ocular mirror.

Still another object of the present invention is to provide an inspection device for cavities, which device comprises a cylindrical means and an inspection mirror which consists of a first means whose fore end holds the inspection mirror in tiltable fashion and a second means whose fore end engages with said inspection mirror, said inspection mirror means extending along the side of said cylindrical means with the base thereof being rotatably installed on said cylindrical means and either of said first or second means being axially slidable relative to said cylindrical means, whereby said inspection mirror can be rotated at a practically fixed position and/or angular displacement thereof is rendered possible.

An additional object of the present invention is to provide an inspection device for cavities, wherein said cylindrical means is further equipped with an ocular mirror means on which an ocular mirror cooperating with said inspection mirror, to wit, the object mirror, is provided in displaceable fashion, whereby one can easily inspect all places of the inside of mouth cavity or the like by oneself.

An additional object of the present invention is to provide an inspection device for cavities, wherein the fore end of said cylindrical means is equipped with an illumination means, whereby a place-to-be-inspected can be lighted brightly through or not through said inspection mirror or object mirror.

An additional object of the present invention is to provide an inspection device for cavities, wherein said inspection mirror means or object mirror means is detachably installed on said cylindrical means so that the device can be utilized sanitarily and efficiently. Several different kinds of inspection mirror means or object mirror means, including children's or infants' small-sized ones, can be attached alternatively to a common cylindrical means. When the device is further provided with an ocular mirror means, after detaching the object mirror means, the mouth cavity, tooth, gum, throat, eyeball, nasal cavity as well as other body parts can be visually inspected with the aid of the ocular mirror means, for instance, such as lip, face, etc. and can be lighted brightly and inspected in detail by oneself.

An additional object of the present invention is to provide an inspection device for cavities, wherein said inspection mirror means or object mirror means is made shiftable along said cylindrical means, whereby the distance from the fore end of the inspection mirror means or object mirror means to the base end of said cylindrical means can be shortened when the device is not in so as to be convenient for storage.

An additional object of the present invention is to provide an inspection device for cavities, wherein said ocular mirror means is provided with a base plate which is detachably installed on the base of said cylindrical means and holds the cylindrical means, when installed, in an upright position, whereby the cylindrical means with the object mirror means thus mounted thereon can be demounted from the ocular mirror means and used independently so that it is possible for persons to inspect not only themselves but also others, for instance, parents can inspect their children, while when the device is not in use, the cylindrical means can be held in an upright position without particularly providing any stand.

Yet another object of the present invention is to provide an inspection device for cavities, wherein said ocular mirror is composed by connecting the ocular mirror with the base plate by means of a universal joint, whereby not only the ocular mirror can be angularly displaced in relation to said cylindrical means and object mirror means but also the distance from the cylindrical means or the object mirror means, particularly the distance from the object mirror, can be optionally adjusted so that anyone can inspect an intended place in a natural posture suitable for him despite variations in face sizes, the relative position of fore-teeth and back-teeth, the individual difference of eyesight, etc.

BRIEF DESCRIPTION OF THE DRAWING

FIGS. 1 through 4 of the appended drawings are diagrams illustrating ways of handling a dental mirror and a handmirror when self-inspecting one's teeth using a conventional dental mirror, wherein:

FIG. 1 is a schematic side view of the position of the device at the time of inspecting the back-teeth;

FIG. 2 is a schematic plan view of the same position of the device at the time of inspecting the back-teeth shown in FIG. 1;

FIG. 3 is a schematic side view of the position of the device at the time of inspecting the lower fore-teeth; and FIG. 4 is a schematic plan view of the same position of the device at the time of inspecting the lower fore-teeth shown in FIG. 3;

FIG. 5 is a partially cutaway front view illustrating one simplified embodiment of the inspection device according to the present invention.

FIG. 6 is a partially cutaway front view illustrating a modified embodiment of the same device as disclosed in FIG. 5.

FIGS. 7 through 23 of the appended drawings are diagrams illustrating a first embodiment which is most typical of the inspection device according to the present invention, wherein:

FIG. 7 is a longitudinal sectional view of the inspection device of the present invention;

FIG. 8 is a side view, partly broken away, of the device of FIG. 7 taken from the left side of FIG. 7;

FIG. 9 is a side view, partly broken away, of the same device as in FIG. 7 taken in the same way as in FIG. 8, which illustrates the state of the object mirror member 20 which has been turned 180° from the position shown in FIG. 8 and the ocular mirror member 50 has been lowered;

FIG. 10 is a transverse sectional view taken along the line X—X in FIG. 9;

FIG. 11 is a front view, partly broken away, of the inspection device, which illustrates the state of the object mirror member 20 when lowered to the storing position;

FIG. 12 is a front view which illustrates the remaining parts of the inspection device after demounting the object mirror member 20 therefrom;

FIG. 13 is a front view of the object mirror member 20 as demounted from the inspection device;

FIG. 14 is a front view, partly broken away, of the remaining part of the inspection device after demounting the ocular mirror member 50 therefrom;

FIG. 15 is a front view which illustrates the ocular mirror member 50 as demounted from the inspection device;

FIG. 16 is an enlarged longitudinal sectional view of the upper part of the object mirror member 20, which illustrates the state of tilting of the object mirror 25;

FIG. 17 is a side view of the upper part of the object mirror member 20 shown in FIG. 16 as taken from the back of the object mirror 25;

FIG. 18 is a sectional view taken along the line XVIII—XVIII in FIG. 16;

FIG. 19 is a sectional view taken along the line XIX—XIX in FIG. 16;

FIG. 20 is a sectional view, on an enlarged scale, taken along the line XX—XX in FIG. 14;

FIG. 21 is a longitudinal sectional view, which illustrates a modification of the object mirror member 20

FIG. 22 is a front view illustrating the inspection device in the state of being stored, wherein the cover 80 is shown in longitudinal section; and FIG. 23 is a side view taken from the right side of FIG. 22, wherein the cover 80 is shown in longitudinal section.

FIGS. 24 through 30 illustrate a second embodiment of the inspection device for cavities according to the present invention, wherein:

FIG. 24 is a front, partially sectional, view of the inspection device of the present invention;

FIG. 25 is a side view taken from the left side of the device shown in FIG. 24;

FIG. 26 is a sectional view taken along the line XXVI—XXVI in FIG. 24;

FIG. 27 is a side view which illustrates the remaining part of the inspection device after demounting the ocular mirror member 150 therefrom;

FIG. 28 is a front view which illustrates the ocular mirror member 150 as demounted from the inspection device;

FIG. 29 is a side view taken from the right side of the ocular mirror member shown in FIG. 28; and FIG. 30 is a plan view of the ocular mirror member shown in FIG. 28.

FIGS. 31 through 34 illustrate a third embodiment of the inspection device for cavities according to the present invention, wherein:

FIG. 31 is a front view, partly broken away, which illustrates the inspection device;

FIG. 32 is a side view taken from the left side of the inspection device shown in FIG. 31, wherein the upper part is omitted;

FIG. 33 is a sectional view taken along the line XXXIII—XXXIII in FIG. 31; and

FIG. 34 is a sectional view taken along the line XXXIV—XXXIV in FIG. 31; and

FIGS. 36 through 41 are drawings illustrating a fifth embodiment of the inspection device for cavities according to the present invention, wherein:

FIG. 36 is a front view of the inspection device;

FIG. 37 is a side view taken from the right side of the inspection device shown in FIG. 36;

FIG. 38 is a front view which illustrates an example of a modification of the upper part of the object mirror member 420;

FIG. 39 is a side view of the object mirror member 420 shown in FIG. 38;

FIG. 40 is a front view which illustrates another example of a modification of the upper part of the object mirror member 420; and FIG. 41 is a side view of the object mirror member shown in FIG. 40.

FIGS. 42 through 46 are drawings illustrating a way of operating the inspection device for organic cavities according to the present invention in inspecting one's own teeth using the fifth embodiment of the invention as the inspection device, wherein:

FIG. 42 is a schematic representation of a side view of the position of the device at the time of inspecting the backteeth, which corresponds to that of the conventional device shown in FIG. 1;

FIG. 43 is a plane figure a plan view of the position of the device at the time of inspecting the backteeth, which corresponds to that of the conventional device shown in FIG. 2;

FIG. 44 is a side view of the position of the device at the time of inspecting the lower fore-teeth, which corresponds to that of the conventional device shown in FIG. 3;

FIG. 45 is a plan view of the position of the device at the time of inspecting the lower fore-teeth, which corresponds to that of the conventional device shown in FIG. 4; and FIG. 46 is a side view which illustrates another way of operating the device at the time of inspecting the lower fore-teeth which is different from the way shown in FIG. 44.

DETAILED DESCRIPTION OF THE INVENTION

Figure 1:
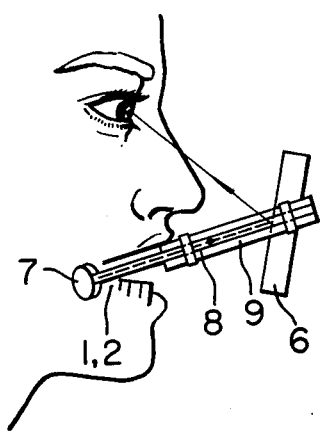

FIG. 5 illustrates one simplified embodiment of the inspection device for cavities according to the present invention. This inspection device comprises a body 510 and an inspection mirror 525. The body 510 receives the lower part of a post 523 so that the post can rotate around the axis thereof. The inspection mirror 525 is mounted tiltably on the upper end of the post 523. The post 523 is provided with an operating sleeve 522 which is slidable in the direction of the axis of the post 523, said operating sleeve being secured to a rod 541 engaged with the inspection mirror 525. Accordingly, when holding the body 510 and turning the operating sleeve 522 with the fingers the inspection mirror 525 rotates, and when shifting the operating sleeve 522 in the direction of the axis of the body 510 the inspection mirror tilts.

FIG. 6 illustrates one modification of the same embodiment as shown in FIG. 5. In this inspection device, the body 510 is further provided with an ocular mirror 561 which is tiltable in two directions and the post 523 is further provided with a lamp 513. The other parts are all the same as in the device of FIG. 5. The inspection device disclosed herein is advantageous in that it permits inspection of the parts to be inspected under bright illumination from the lamp 513 and for instance, when persons try to inspect their own teeth, this can be achieved by this inspection device alone without the aid of any other handmirror. The above explanation was made taking the theoretical case of the inspection device according to the present invention. A further theoretical explanation of the present invention will be made as follows. Various means such as worm gear, cam, link and the like may be employed for the purpose of tilting the inspection mirror relative to the body. In other words, any means is available for this purpose which is capable of tilting the inspection mirror by the relative movement of a first member to hold the inspection mirror to a second member to engage with the inspection mirror. The relative movement of the first member to the second member referred to herein naturally includes not only a relative axial movement therebetween but also a relative rotation therebetween, and further may include a composite movement of said axial movement and rotation and other optional relative movements. And the operation of said relative movements may be effected not only by means of the operating sleeve but also by means of a lever, for instance, such as the trigger of a pistol. In addition thereto, other optional operation means may be employed for that purpose. Furthermore, the lamp may be installed in a recess provided in the post, and an optical fiber may be used in lieu of said lamp. Any means may be available in the present invention which functions effectively as illumination means. And the illumination means may assume a construction such that no matter what sort of light source is employed or how it is disposed, the parts to be inspected are illuminated by the light cast directly from the light source or the light once reflected by the inspection mirror.

Figure 20:

Shown in FIGS. 7 through 23 is a first embodiment which is most typical of the inspection device for organic cavities according to the present invention. In these diagrams, the reference numeral 10 denotes a cylindrical member which is most precisely illustrated in FIG. 12, 20 denotes an inspection mirror member or an object mirror member which is most precisely illustrated in FIG. 13, and 50 denotes an ocular mirror member which is most precisely illustrated in FIG. 15.

The cylindrical member 10 is composed of an inner cylinder 11 which is devised to accommodate a battery therein and an outer cylinder 12 which fits on the outside of said inner cylinder 11. On the fore end of the inner cylinder 11 is equipped a lamp 13 which is electrically connected to said battery, and a cover 14 for this lamp 13 is fastened to the fore end of the inner cylinder 11. Near the base of the inner cylinder 11 is provided a rotary switch 15 for lighting said lamp 13. The inner cylinder 11 is preferably of water proof construction. The outer cylinder 12 extends along the full length of the inner cylinder 11 except for the lamp cover portion 14. The outer cylinder 12 is provided with an operating annular groove 16 formed on the circumference thereof near the fore end thereof and a storing annular groove 17 formed on the circumference thereof near the longitudinal middle of the same and closer to the base than the groove 16. The portion of cylinder 12 that extends from said storing annular groove 17 to the lower end of the base is supposed to serve as the handle. In the vicinity of the lower end or base of the outer cylinder 12 is formed a pair of openings 18 for the purpose of operating the switch 15, and above these openings 18 is formed a stopper projection 19.

The inspection mirror member or object mirror member 20 is composed of a support member 21 having an operating sleeve 22 which is slidably fitted on the outer cylinder 12 of the cylindrical member 10 in detachable fashion and a rod 41 having a rod end 42 which is guided by said support member 21 and fits in the operating annular groove 16 or the storing annular groove 17 of the outer cylinder 12 of the cylindrical member 10 in detachable fashion.

On the support member 21 is formed a support 23 having a specified length which extends upwardly from the side of an operating sleeve 22, and on the fore end of said support 23 is installed an inspection mirror or object mirror holder 24 holding an inspection mirror or object mirror 25 by means of a pin 26 so that said object mirror holder is capable of tilting around said pin 26. Said operating sleeve 22 is devised so as to be rotatable around the outer cylinder 12 and to be slidable in the axial direction thereof. Besides, this sleeve 22 is devised to fit on the outer cylinder 12 of the cylindrical member 12 in slidable fashion while retaining an appropriate frictional force in relation to the outer cylinder 12 so that it can stand still at an optional position. This frictional force can be obtained from the reaction force of the rod end 42 against the annular groove 16 as well as from the dimensional co-relation between the bore of the operating sleeve 22 and the outer diameter of the outer cylinder 12. The lower half of the outer wall of the operating sleeve 22 is provided with a surface which is not smooth in order to facilitate the operation at the time of rotating or axially sliding the operating sleeve 22. On the inner wall of the support 23 is formed a guide groove 27 which extends lengthwise from the upper end from a position inwardly of the pin 26. This guide groove is so formed that it increases in depth gradually from about the middle of the length of the support 23 toward the lower part thereof to form an inclined guide groove 28, and near the base of the support 23 disposed further below, it becomes a penetrating groove 29 which penetrates the inner and outer walls of the support 23. On the support 23 are further provided a pair of projections 31 facing each other which are disposed near the lower part of said inclined guide groove 28 for the purpose of holding the rod 41 within the guide groove 27 lest it should slip out of the guide groove 27 at the time when the inspection mirror member or object mirror member 20 is demounted from the cylindrical member 10 as illustrated in FIG. 13. On the back of the inspection mirror or object mirror holder 24 are formed a longitudinal groove 32 and an engaging groove 33.

On the other end of the rod 41 opposite to said rod end 42 is formed a rod slide 43 which extends parallel to the pin 26, and this rod slide 43 is inserted in the engaging groove 33 of the inspection mirror or object mirror 65 holder 24 and engages therewith. The middle part of the rod 41 extending from the rod slide 43 to the rod end 42 is accommodated in the logitudinal groove 32, guide groove 27 and inclined guide groove 28, whereby the rod 41 is incorporated into the support member 21. The base of the rod 41 connecting to the rod end 42 is bent into almost U-shape thereby forming a knob 44, said knob projecting outside across the outer wall of the support 23 through the penetrating groove 29 of the support 23.

The inspection mirror member or object mirror member 20 as described above is installed on the cylindrical member 10 in the following way. The operating sleeve 22 is slidably fitted in the outer cylinder 12, and the rod end 42 is engaged with the operating annular groove 16. At this time, the operating sleeve 22 is capable of rotating around the outer cylinder 12 and is also capable of sliding in the direction of the axis thereof. The rod end 42 does not move in the direction of the axis of the outer cylinder 12, but it is capable of rotating around the outer cylinder 12. When the operating sleeve 22 is pulled downward to the position, illustrated in FIG. 7, the knob 44 comes to be located in the upper part of the penetrating groove 29 and the rod slide 43 is located at the right extremity of the engaging groove 33, whereby the angle of tilting of the inspection mirror or object mirror 25 becomes the minimum $\alpha$min. as indicated by a solid line in FIG. 16. On the contrary, when the operating sleeve 22 is pulled upward to the position illustrated in FIG. 14, the knob 44 comes to be located in the lower part of the penetrating groove 29 and the rod slide 43 is located at the left extremity of the engaging groove 33, whereby the angle of tilting of the inspection mirror or object mirror 25 becomes the maximum $\alpha$max. as indicated by a double-dotted line in FIG. 16. The vertical stroke of the operating sleeve 22 necessary for tilting the inspection mirror or object mirror 25 within the range of from $\alpha$min. to $\alpha$max. is expressed by S in FIG. 14.

The inspection mirror member or object mirror member 20 is devised such that, at the time it is not in use, the distance from the upper end thereof to the lower end of the cylindrical member 10 can be shortened in the following way. That is, inasmuch as the knob 44 allows elastic deformation thereof and said elastic deformation is permitted by the provision of the inclined guide groove 28, the operating sleeve 22 can be pulled downward upon disengaging the rod end 42 from the operating annular groove 16 by pulling the knob 44 upward. That is, the lower end of the operating sleeve 22 contacts with the stopper projection 19 formed on the outer cylinder 12, whereby the operating sleeve 22 is prevented from moving downwardly, and at this position the rod end 42 fits in the storing member groove 17 whereby the inspection mirror member or object mirror member 20 is held in this storing position. In order to bring the inspection mirror member or object mirror member 20 from the storing position to the using position, it suffices to pull only the operating sleeve 22 upwardly by applying a force slightly stronger than normal force. In this way, inasmuch as the upper side of the storing annular groove 17 is formed in tapered fashion as illustrated in FIG. 11, the rod end 42 disengages from the storing annular groove 17 spontaneously, and soon fits in the operating annular groove 16. As a result, the inspection mirror member or object mirror member 20 is moved to the using position.

As illustrated in FIG. 21, on the support 23 may be formed a blind groove 29a in lieu of said penetrating groove 29a, and for the rod 41 a spherical tip 42a may be formed on the rod end 42. In this embodiment the knob 44 is omitted. In this way, by merely pulling upward or downward the operating sleeve 22 by a force stronger than normal, the spherical tip 42a can be disengaged from the operating annular groove 16a without pulling the knob 44 as described in the foregoing. Besides, instead of forming the spherical tip 42a on the rod end 42, the rod 42 may be formed by smoothly curving into, for instance, U-shape or L-shape.

The ocular mirror member 50 is composed by conjoining a base plate 51 having a hole 52 devised to receive the base of the cylindrical member 10 detachably therein and an ocular mirror holder 61 holding an ocular mirror 62 by means of a ball joint 71.

The hole 52 formed in the base plate 51 may be designed either for pressure-fitting or for screw-fitting of the base of the cylindrical member 10 therein; the point is that the cylindrical member should be held in upright posture when the base thereof is set in said hole 52. The base plate 51 is, as illustrated in FIG. 10, formed to have its end portion with the hole 52 gently curved so that the lower half of the cylindrical member 10 can be firmly gripped without being obstructed by the edge of the base plate 51 at the time of rotating operation or axially sliding operation of the operating sleeve 22 by holding the cylindrical member 10 by hand. On the base plate 51 is provided a lower arm 53 which rises almost perpendicularly on said plate and then bends to extend almost horizontally in the direction of the end portion of the plate opposite to said curved end portion, said lower arm 53 being provided with a lower ball 54 formed on the fore end thereof. The base plate 51 is further provided with a step portion 55 along its edge excluding said curved end portion, and along this step portion 55 are formed bilateral linear projections overhanging from both sides of the base plate 51.

On the ocular mirror holder 61 is formed an upper arm 63 which rises almost perpendicularly on said holder and then bends to extend almost parallel to the ocular mirror 62, said upper arm 63 being provided with an upper ball 64 formed on the fore end thereof. The ocular mirror 62 consists of a concave mirror so as to magnify the object for the sake of inspection to the minutest details.

The ball joint 71 is composed by disposing face to face a pair of supports 72 having spherical hollows, respectively, for accommodating the lower ball 54 and the upper ball 64 in each end in slidable fashion and conjoining both supports 72 at their central part. The construction of the joint of the supports 72 is such that on one support is fastened a screw bolt 73 which extends from said support to the other, on the other support is provided a tapped hole to engage with said screw bolt 73, and the screw bolt 73 is supposed to be driven by a dial 74. The dial 74 is fitted on the circumference of the screw bolt 73 in the interstice of both supports 72, and the key of the bolt 73 fits in the key way of the dial 74. In this way, by turning the dial 74 the interstice of both supports 72 can be widened and narrowed, and accordingly, the lower bolt 54 and the upper ball 64 accommodated in between both supports can be compressed between both supports under an appropriate pressure. The ocular mirror holder 61 is therefore movable unrestrictedly in all directions so as not to collide with the cylindrical member 10 and the base plate 51 thereby changing the position as well as the posture thereof, and moreover it can be brought to a standstill at an optional position or in an optional posture.

As illustrated in FIG. 9, a rotatable collar 65 can be provided at a position on this side of the upper ball of the upper arm 63. In this way, on the occasion of operating the ocular mirror holder 61 so as to slide along the edge 75 of the end portion of support 72 while keeping the upper arm 63 in contact with said edge 75, the collar 65 comes in contact with the edge 75 and rotates, and accordingly, the frictional force at the time of contact between the upper arm 63 and the edge 75 can be sharply reduced compared with the case where the collar 65 is not provided, resulting in the advantage that the operation of the ocular mirror holder 61 becomes very easy. The same is true of the lower arm 53, as well as the upper arm 63.

As a means for holding the ocular mirror holder 61 on the base plate 51, in addition to the above described ball joint 71, a flexible tube for use in a desk-lamp type lighting equipment or a rubber tube with lead wire inserted therein, etc. can be utilized.

Figure 22:
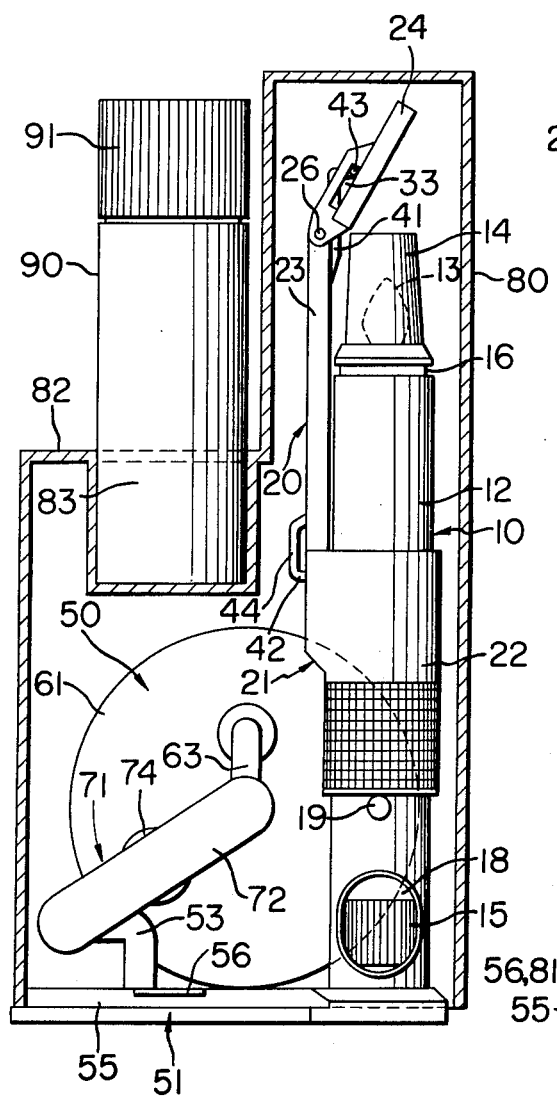
Figure 23:
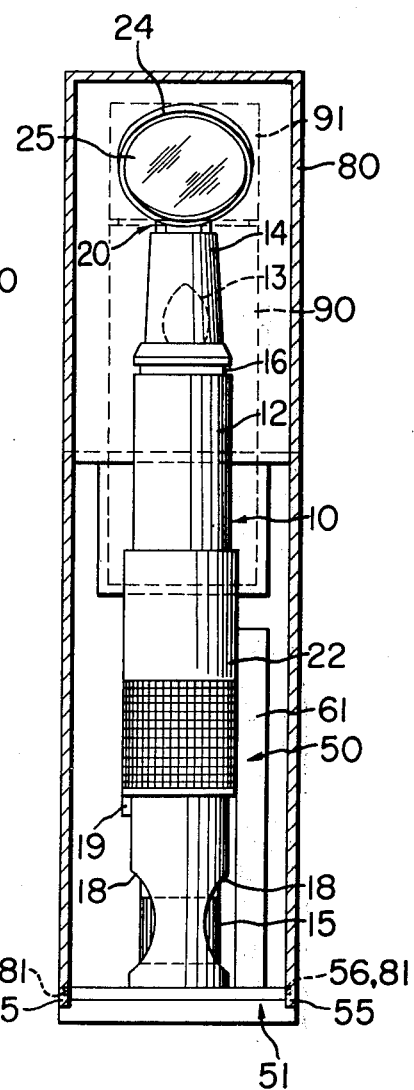

This inspection device is, as illustrated in FIGS. 22 and 23, equipped with a cover 80 for the purpose of storage. The opposing sidewalls or the cover 80 are provided with a pair of concave grooves 81 to cooperate with the pair of linear projections 56 of the base plate 51, said concave grooves 81 being bilaterally formed in the lower end of the cover 80. On the occasion of installing this cover 80, the object mirror member 20 is first displaced to the storing position by lowering it in relation to the cylindrical member 10 and the length extending from the upper end of the object mirror member 20 to the lower end of the cylindrical member 10 is shortened. Next, by operating the ocular mirror member 50, particularly the ball joint thereof, the back of the ocular mirror holder 61 is brought in contact with the operating sleeve 22 of the object mirror member 20. Under such a condition, when the cover 80 is put on the device from above and is press fitted finally, the lower end of the cover 80 elastically deforms and the linear projections 56 of the base plate 51 fit in the concave grooves 81 thereof, whereby the cover 80 comes to be fastened on the base plate 51. In order to remove the cover 80, it suffices to press towards each other the lower parts of the end walls that do not contain the concave grooves 81, thereby narrowing the distance between the end walls. In this way, the sidewalls of the cover 80 are elastic deformed outwardly and the concave grooves 81 are disengaged from the linear projections 56, whereby the cover 80 can be removed. On the upper part of the cover 80 is formed a notch 82, and in the bottom face of this notch 82 is formed a recess 83.

The present inspection device is mostly used in an humid atmosphere; for instance, in the case of inspecting the mouth cavity, the object mirror 25 is inserted in the mouth cavity, and not only that, this device is generally placed within a bathroom. As a result, the object mirror 25 and the ocular mirror 62 are apt to become cloudy with moisture, thereby rendering it difficult to inspect the image. Therefore, the present inspection device is equipped with a bottle 90 containing a liquid for preventing these mirrors from getting cloudy. This anti-cloud liquid containing bottle 90 is of a construction such that when the cap 91 is removed and a slight pressure is applied to the body of the bottle so as to push out the contents thereof, the anti-cloud liquid contained therein is dripped from opening provided with small pores. The anti-cloud liquid containing bottle 90 has its base press fitted in a recess 83 formed in the cover 80, and can be always stored together with the cover 80 in a body.

Shown in FIGS. 24 through 30 is a second embodiment of the present invention. In these figures, the parts which are similar to those of the afore described first embodiment are denoted by the respective reference numeral used in said first embodiment plus 100, and explanation hereunder will be made mainly on the parts which are different from those in the first embodiment.

In the vicinity of the lower part of the battery storing cylinder 111 is fastened a detachable collar 112. This detachable collar 112 is provided with a chuck groove 116. On an outer edge of a flange 117 on the collar 112 is installed a downwardly extending hook 118 with a pole 119 on the tip thereof. On the lower end of the battery storing cylinder 111 is provided a rotary switch 115 whose diameter is somewhat smaller than the outer diameter of said cylinder 111.

Figure 24:
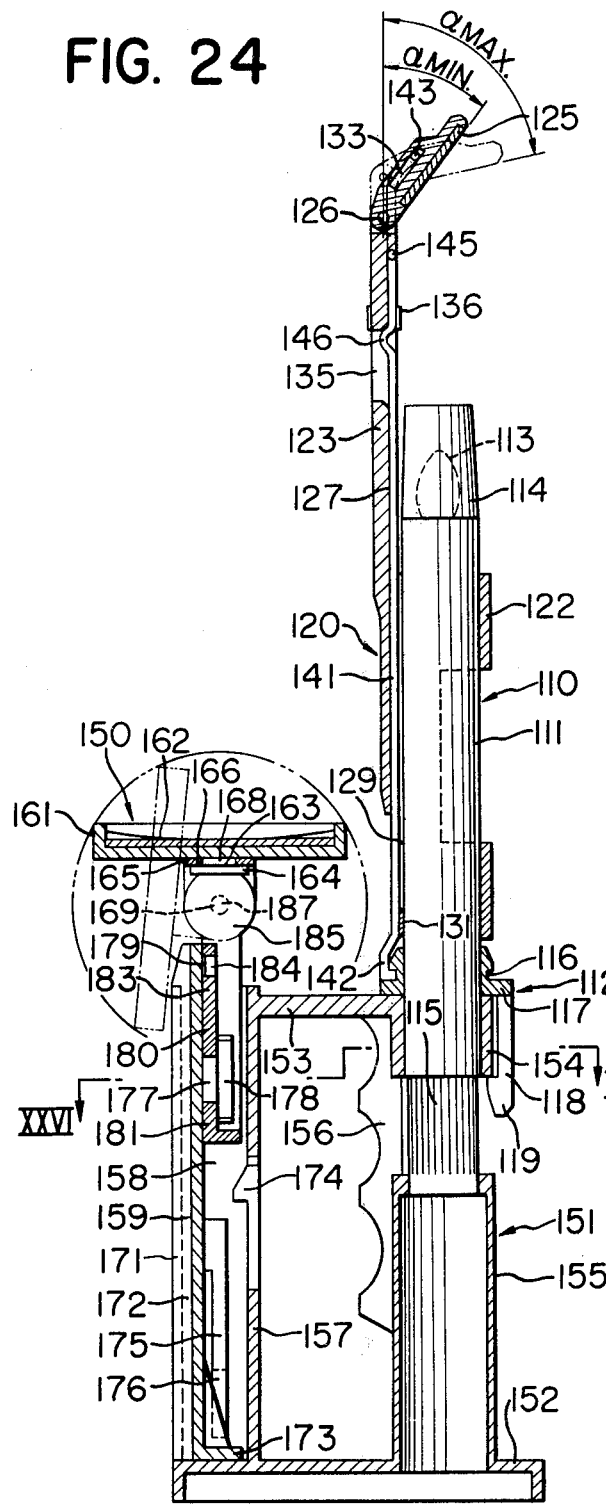

The upper tip of the rod 141, for the purpose of tilting the object mirror 125 by vertically moving the operating sleeve 122, is bent horizontally as illustrated in FIG. 25 and is slidably fitted in the tilting groove 133 on the back of the object mirror 125 as the rod slide 143. One end of the rod slide 143 extends downwardly while forming a small arc, and slightly hangs down from around the hinge pin 126 as illustrated in FIG. 24. Next, referring to FIG. 27, within the tilt controlling groove 134 formed in the upper part of the support 123, the rod 141 turns at a right angle to form a rod stopper 145 and soon turns downward at a right angle again to fit slidably in the rod groove 127.

As illustrated in FIG. 24, when the side view is taken of the portion between the rod slide 143 and the rod stopper 145, the rod slide 143 is located above and outside the rod stopper 145. As a result, in the case of the device illustrated herein, when the operating sleeve 122 is located at the lower limit, the rod stopper 145 is located at the upper end of the controlling groove 134, and accordingly, the object mirror 125 is slightly tilted centering round the axis of the hinge pin 126.

Figure 27:
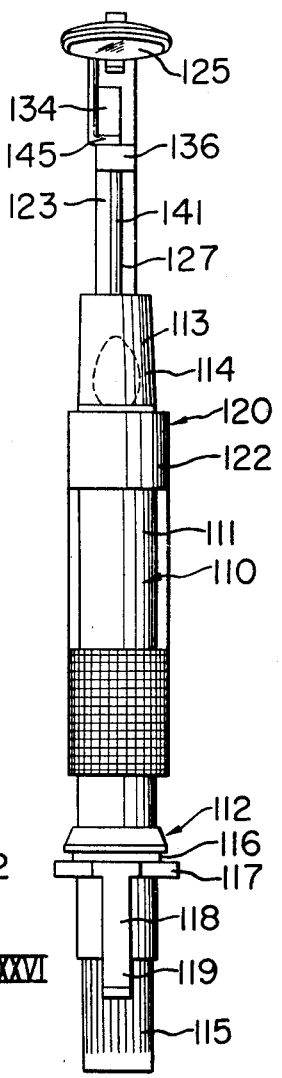

When the vertically movable operating sleeve 122 is located at the upper limit, to wit, when the rod stopper 145 is located at the lower end of the controlling groove 134, as illustrated in FIG. 27, the object mirror 125 tilts sharply to be almost in a horizontal position.

As illustrated in FIG. 24, the rod 141 within the rod groove 127 is provided with a rotation preventive projection 146 which is formed in the middle thereof and fits in the rotation preventive groove 135, and the portion below this projection extends perpendicularly to the lower end along the rod groove 137. The rod end 142 of the rod 141 projects slightly outward along the detachable collar 112 as illustrated in FIG. 24, hangs down thereafter, turns at a right angle to form an L-shape, and slidably fits in the chuck groove 116. The neck band 136 consists of a circular spring as partly cut open, and is press fitted on the support 123 by utilizing its clamping force due to resilience, thereby preventing the rod 141 from slipping out of the groove 127. The same effect may as well be obtained by winding a tape-like band 136 round the support 123.

In the center of the back of the ocular mirror holder 161 is provided a holder stem 163 having a stem flange 164. In the center of the top plate 166 of an inverted channel-shaped hinge 165 is provided the top plate hold 168 having a notch 167, and when this notch 167 is made to confront the stem 163 and the hinge 165 is thrust in the holder 161 sidewardly, by dint of the elasticity of the top plate 166, the notch 167 somewhat opens to hold the stem 163 and the hole 168 slidably engages with the holder stem 163. On the bilateral projections of the inverted channel-shaped hinge 165 is provided the holes 169.

A frame 151 is composed of a frame bed 152 constituting the bottom and an upper frame portion 153 constituting the top. An upper handle 154 is formed on the lower part of the right side of the upper frame portion 153 and a lower handle 155 is formed on the upper part of the right side of the frame bed 152. Besides, a rib 156, used as a finger-hold, is formed on the periphery of both handles. The space between these two handles 154, 155 is maintained to be sufficient for inserting finger tips for operating the rotary switch 115. The left side of the frame 151 are formed of, as illustrated in FIG. 26, a frame wall 157 as inner wall, a pair of frame sides 158 as right and left outer walls, and a pair of frame rails 159 attached to the fore ends of said frame sides 158.

The side of the right extremity of the upper frame portion 153 is provided with a hook groove 160 as illustrated in FIG. 30. The lower end of the battery storing cylinder 111 fits in the inside diameter of the upper handle 154 in slidable fashion. The hook 118 engages with the hook groove 160, and the pole 119 formed on the lower end of the hook 118 develops elastic deformation at the time when the battery storing cylinder 111 is press fitted from above and descends while sliding along the outer periphery of the upper handle 154. Then, the pole 119 catches the lower end face of the handle 154 with a click, whereby the cylindrical member 110 is detachably fastened to the frame 151. The lower end of the rotary switch 115 fits in the upper end of the lower handle 115 in slidable fashion.

The slide grooves 172 of the right and left ends of the slide 171 engage with the aforesaid frame rails 159 in slidable fashion, whereby the slide 171 can slide vertically. A part of the lower end of the slide 171 projects inward at a right angle to form the slide end 173 as illustrated in FIGS. 24 and 25. Around the center of the frame wall 157 is provided a slide stopper 174 having inclined top face and horizontal bottom face which is somewhat bendable from side to side and projects inside slightly from the surface of the wall 157. Accordingly, when the slide 171 is slid upward, the top face of the slide end 173 comes in contact with the level surface of the lower part of projection of the slide stopper 174 in the end and is stopped. FIG. 28 illustrates this state. On the occasion of inserting the slide 171 in the frame 151 from above at the time of assembling, due to contact between the inclined face of the projection of the stopper 174 and the bottom face of the slide end 173, the stopper 174 somewhat bends to provide from the surface of the wall 157, whereby the slide end 173 passes smoothly.

On both ends of the lower part of the inside of the slide 171 are provided the brake arms 175 having a slip 176 on the bottom thereof respectively. These slips 176 slide with fraction along the inner wall surface of the frame side 158 by virtue of resilience thereof, and on account of this appropriate frictional force, even in the case, for instance, where the slide 171 is pulled out upward and then is released from hand, it will be safe from falling hard. From the middle of the upper part of the inside of the slide 171 projects a short shaft 177 having an I-shape head 178. Further above this projecting short shaft 177 is provided a projection 179.

On the support wall 181 of the lower part of the support 180 is provided a major groove 182. This major groove 182 is of dimensions sufficient for enabling the short shaft 177 of the slide 171 and the I-shape head 178 to fit slidably therein when the support 180 is turned sideways by 90°. The upper part of the surface of the support wall 181 to come in contact with the slide 171 protrudes slightly relative to the other part of the surface of said support wall 181, thereby forming a friction wall 183. On this friction wall 183 is provided a minor groove 184 disposed confronting the projection 179 of the slide 171.

On the right and left sides of the support wall 181 are provided the arms 185 perpendicular to the wall 181. In between the friction wall 183 and the arm 185 is provided an interstice 186 as illustrated in FIG. 29, whereby the friction wall and the arm can move freely with each other. The span of the arms 185 is somewhat larger than interspace of the bilateral overhangs of the inverted channel shaped hinge 165. On the arms 185 are provided the stems 187. When the arms 185 are pinched with fingers so as to contract the interspace of arms 185 and are inserted as such in between the bilateral overhangs of the hinge 165 so as to let the stems 187 into the hinge holes 169, the arms engage with the hinges with a click owing to the frictional force of press fitting utilizing the difference between said span of arms and interspace of bilateral overhangs, whereby the ocular mirror 162 can be tilted centering round the stems 187 and, at the same time, can be set at optional positions.

When the support 180 is once laid sideways by turning it by 90° thereby engaging the major groove 182 thereof with the I-shape head 178 of the slide 171 as well as the short shaft 177 and thereafter is raised up perpendicularly by turning it by 90°, the support wall 181 is clamped in between the I-shape head 183 and the slide 171. The friction wall 183 comes in press contact with the slide 171 and generates frictional force. By the action of the minor groove 184 and the projection 179, the angle of tilt of the ocular mirror holder 161, and accordingly the ocular mirror 162, centering on the short shaft 177 as fulcrum is limited to the extent indicated by a dotted line in FIG. 25. By virtue of an appropriate frictional force of the friction wall 183, tilt of said ocular mirror 162 centering on the short shaft 177 as fulcrum can be set at optional positions.

Shown in FIGS. 31 through 34 is a third embodiment of the present invention. Since the device in this embodiment comparatively resembles to that of the second embodiment, the parts which are similar to those of the second embodiment are denoted by the respective reference numerals used in the second embodiment plus 100, and explanation hereunder will be made mainly on the parts which are different from those in the second embodiment.

The rotary switch 215 provided on the lower end of the battery storing cylinder 211 is press fitted in the central opening of the handle 212, and the lower part of the battery storing cylinder 211 is press fitted in the bore of the upper frame portion 253 constituting the top of the frame 251.

The inner wall of the upper end of the handle 212 engages in slidable fashion with the outer wall of the downward boss 254 formed on the end of the upper frame portion 253, and the outer wall of the lower end of the handle 212 engages in slidable fashion with the hole 255 of the frame bed 252 constituting the bottom of the frame 251. Accordingly, the handle 212 is rotatable in between the upper frame portion 253 and the frame bed 252 of the frame 251. Several stoppers 219 equipped on the lower part of the handle 212 are for the purpose of preventing the handle 212 from falling off downward, and the spring action of these stoppers 219 facilitates the insertion of the handle 212 in the hole 255 from beneath the frame bed 252.

The switch 215 of the cylindrical member 210 and the handle 212 rotate in a body, but the battery storing cylinder 212 does not rotate. When the handle 212 is turned by about 90°, the lamp 213 will be switched on or off.

In the lower part of the slide 271 is provided a sidewardly extending T-shape groove 294. The lower shaft 291 of the lever 299 penetrate the longitudinal groove 297 of the groove 294 from the outside and engages with the lever shaft hole 292 of the frame wall 257 of the frame 251 in slidable fashion, and is fastened by the washer 293 lest it should fall out. The guide pin 295 disposed inside the lower arm 290 penetrates the horizontal groove 296 of the groove 294 and engages with the cylinder groove 298 of the frame wall 257 in slidable fashion.

The construction of the support 280 to be installed on the upper part of the slide 271 is the same, in substance, as that of the support 180 described previously; the only point of difference is that the support 280 is installed on the outside of the slide 271. The vertical movement of the slide 271 is effected as follows: the lever arm 290 is shifted from a position indicated by a solid line to a position indicated by a double-dotted line in FIG. 32 by turning the lever arm 290 round the lever shaft 291. Hereupon, the guide pin 295 reciprocates horizontally along the horizontal groove 296 in sliding fashion, whereby the slide 271 comes to be moved upward. The longitudinal groove 297 is for the purpose of accepting the lever shaft 291. The circular groove 298 is for the purpose of defining the upper limit as well as the lower limit of the movement of the lever arm 290.

FIG. 33 illustrates the state of things at the time when the ocular mirror holder 261 has been horizontally tilted. When tilted horizontally as indicated by a double-dotted line, the holder 261 draws near the operating sleeve 222 and the visual field of the ocular mirror 3 becomes wider that much.

Figure 35:
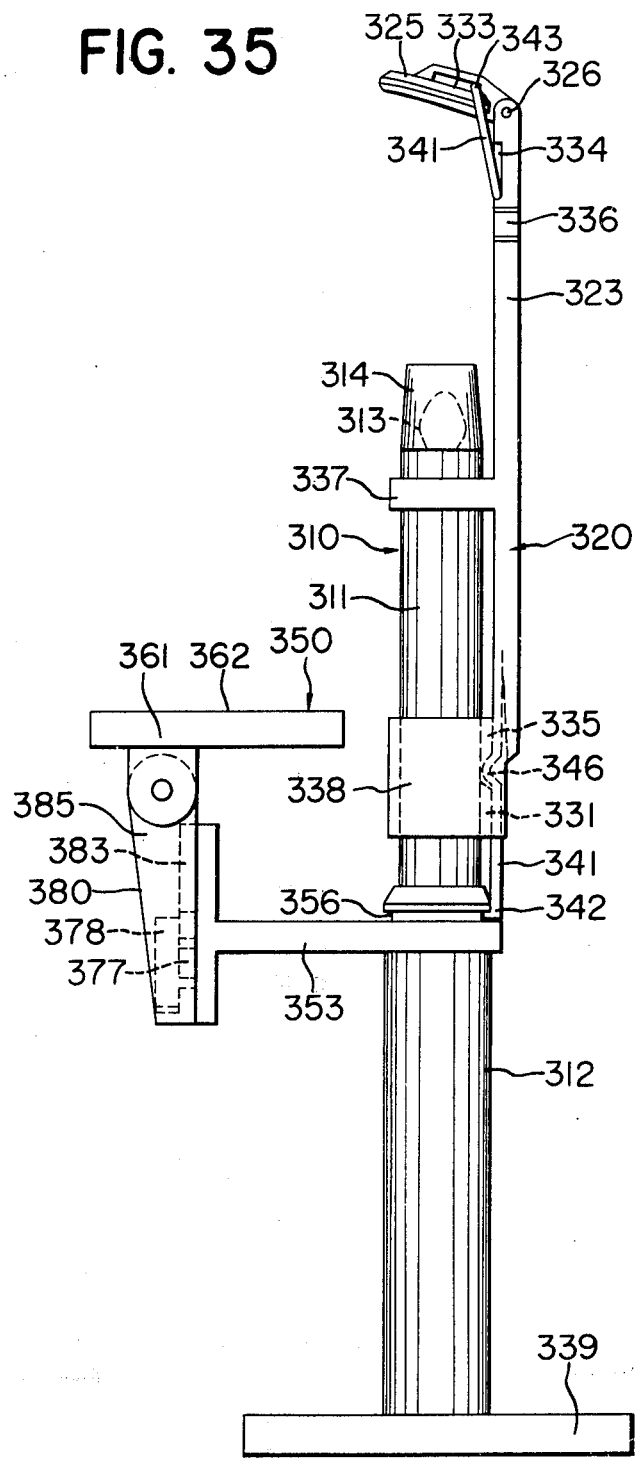
FIG. 35 is a front view of a fourth embodiment of the inspection device for cavities according to the present inventions.
Figures 38, 39:
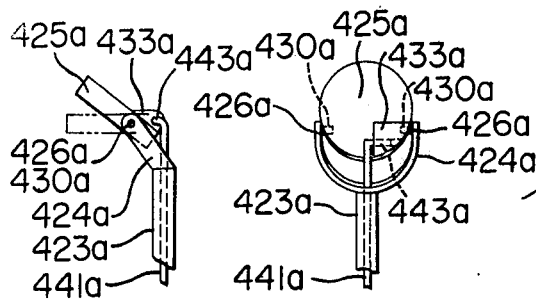

Shown in FIG. 35 is a fourth embodiment of the present invention. Since the device in this embodiment comparatively resembles to that in the third embodiment, the parts which are similar to those of the third embodiment are denoted by the respective reference numerals used in the third embodiment plus 100, and explanation hereunder will be made mainly on the parts which are different from those in the third embodiment.

On the middle part of the support 323 of the object mirror member 320 is installed the upper collar 337, and on the lower end of the same support is installed the lower collar 338, said collars fitting slidably on the cylindrical member 310. In the lower part of the rod 341 is provided the rotation preventive projection 346, and this projection 346 is accomodated in the rotation preventive groove 335 of the lower collar 338.

On the battery storing cylinder 311 of the cylindrical member 310 is press fitted the hole of the sidewardly extending T-shape bracket 353. On the bracket 353 is fixed the support 380 similar to the one described previously. On the lower end of the handle 312 is provided the base plate 339 for the handle incorporated therewith.

When the handle 312 is gripped and the bracket 353 is slightly turned in relation to the handle 312, the lamp 313 is switched on. Through combination of the support 380 with the bracket 353 and the support 380 with the ocular mirror holder 361, tilting in two directions as in the foregoing embodiments can be effected.

The reason for providing the rotation preventive projection 346 is that, should it not be provided, at the time when the rod end 342 moves along the chuck groove 356, the rod 341 will give rise to rotation centering around the axis of the rod per se and the rod end 342 will be disengaged from the chuck groove 356, and the provision of said projection 346 is for the purpose of preventing this disengagement.

Shown in FIGS. 36 through 41 is a fifth embodiment of the present invention. Since the device in this embodiment comparatively resembles to that in the preceding fourth embodiment, the parts which are similar to those of the fourth embodiment are denoted by the respective reference numerals used in the fourth embodiment plus 100, an explanation hereunder will be made mainly on the parts which are different from those in the fourth embodiment.

The upper stopper 418 and the lower stopper 419 are fastened to the storing cylinder 411 for the cylindrical member 410, and in between these two stoppers the upper support 437 and lower support 438 of the support 423 for the object mirror 425 are slidably engaged with the storing cylinder 411.

The rod 411 between the rod slide 443 and the rod stopper 445 is inclined at an angle of about 15° with the rod stopper as its starting point when viewed from the side as illustrated in FIG. 36 and, as a result, the object mirror 425 is inclined at an angle of about 35° with the hinge pin 426 as its axis of rotation. At the time when the rod stopper 445 is located in the upper end of the tilt controlling groove 434, the object mirror 425 comes to be inclined at an angle of about 35°. At the time when the rod stopper 445 is located in the lower end of said groove 434, the object mirror 425 is inclined at an angle of about 90° to become horizontal state as indicated by a double-dotted line in FIG. 36.

The rod 441 within the rod groove 427 of the support 423 extends perpendicularly to the lower end, and a bit of the rod end 442 bends at a right angle, passes along the rod groove 439 of the operating collar 422 which slidably engages with the battery storage cylinder 411, and fits in the rod hole 440. 460 denotes a tilting lever. When the tip of this tilting lever 460 is slightly moved upward and downward by the thumb while holding the handle 412 by the middle binder, third finger, small finger and the palm, the ocular mirror 462 can be set at a desired angle of inclination with the aid of the stem 487 working as fulcrum. 416 denotes a switch knob of the switch 415, and when this switch knob is turned by about 90°, the switch 415 will be on or off.

FIGS. 38 through 41 illustrate examples of modification of tilting mechanism for the object mirror 425. In the case of a modification shown in FIGS. 38 and 49, a shallow U-shape holder 429a is equipped on the fore end of the support 423a, and by fitting the pin shaft 426a equipped on the two tips of holder 424a in the holes of the bearings 423a provided on the periphery of the object mirror 425a, the object mirror is supported. A fit of the fore end of the rod 441a accommodated in the support 423a having channel-shaped or tubular section bends at a right angle to form the rod end shaft 443a which fits in the bearing 433a installed on the back wall of the object mirror 425a corresponding to the fore end of the support 423a, and the object mirror 425a tilts with the pins shafts 426a of the tips of the holder 424a as fulcrum.

Figures 40, 41:
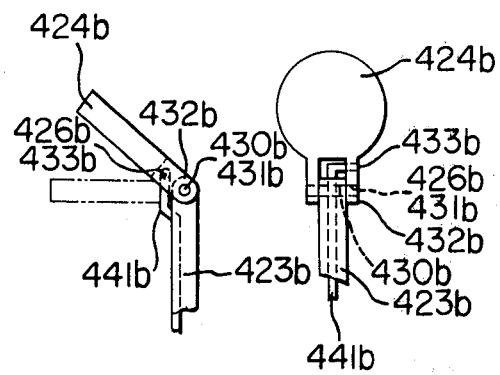

In the case of a modification shown in FIGS. 40 and 41, a hinge with concave groove 432b is formed on the end of the object mirror holder 424b, said concave groove being rather deep, the fore end of the rod 441b is supported on the rod bearing 433b of the concave groove 432b, a pin hole 430b is formed in the fore end of the support 423b, and the holder 424b is rotatably supported by means of said pin hole 431b of hinge with concave groove 432b and hinge pin 426b. By virtue of vertical movement of the rod 441b, the object mirror 425b tilts with the hinge pin 426b as fulcrum.

In the case where a conventional light source, instead of the pencil light used as a lamp in the foregoing embodiments, is set on a separated place and employed as the lighting member by inducing the light to the support by means of an optical fiber, the same effect can of course be obtained.

Next, how to handle an inspection device according to the present invention will be described in the following with reference to FIGS. 42 through 46 dealing with the device of the fifth embodiment. In this context, the way of handling the devices in the first through fourth embodiments is fundamentally the same as that in the case of the fifth embodiment to be described later on. As for some points of difference, they are easy to understand from the foregoing descriptions of the construction of the device in each embodiment, and therefore, explanation thereof will be omitted.

When the handle 412 is held and the battery storing cylinder 411 is twisted a little by applying the thumb to the switch knob 416, the switch 415 becomes on and the lamp 413 is lit. While holding the handle 412 so as to locate the ocular mirror 462 above the handle, the object mirror 425 is inserted in the mouth. On the occasion of thus inserting, said mirror is held almost perpendicular to the mouth. Then, the object mirror 425 is positioned near the tooth-to-be-inspected, and the angle $\beta$ included by the ocular mirror 462 and the ocular mirror bracket 485 is first determined to see that the object mirror 425 be reflected in the center of the ocular mirror 462 by tilting the ocular mirror 462. Next, upon vertically moving the operating collar 422, said vertical movement is transmitted to the rod 441. The vertical movement of the rod 441 is converted into a slide movement of the object mirror 425 along the tilting groove 433, and the object mirror 425 starts a tilting movement with the pin 426 as fulcrum. The tilting angle $\alpha$ (angle of inclination) of the object mirror 425 relative to the support 423 is determined to see that the object tooth be reflected in the ocular mirror 462. In this state, the operating collar 422 is rotated, and this rotation is transmitted to the support 423, and accordingly to the object mirror 425, with the aid of the rod 441, whereby the position of the object mirror 425 is adjusted so as to be most convenient for inspecting the posture of tooth.

In the case of inspecting a back tooth, the angle of inclination $\alpha$ of the object mirror 425 suffices to be narrow. The closer is the object mirror 425 to the fore-teeth, the wider is made the angle $\alpha$ by lowering the operating collar 422. In the case of inspecting the back of a lower fore-tooth, the operating collar 422 is lowered to the lowermost and the angle $\alpha$ is widened to be close to 90°. In the case of inspecting the back of an upper fore-tooth, it is appropriate to set the angle α at about 45°.

As to the front of the fore-teeth, one is used to viewing them. However, in the case of inspecting it by means of the inspection device of the present invention, it suffices to reflect the surface of the fore-teeth directly in the ocular mirror by generously widening the angle of inclination β of the ocular mirror 462 to almost 135° and displacing the surface of the ocular mirror 462 to be practically parallel to the handle 412, support 423 and battery storing cylinder 411.

Figure 46:
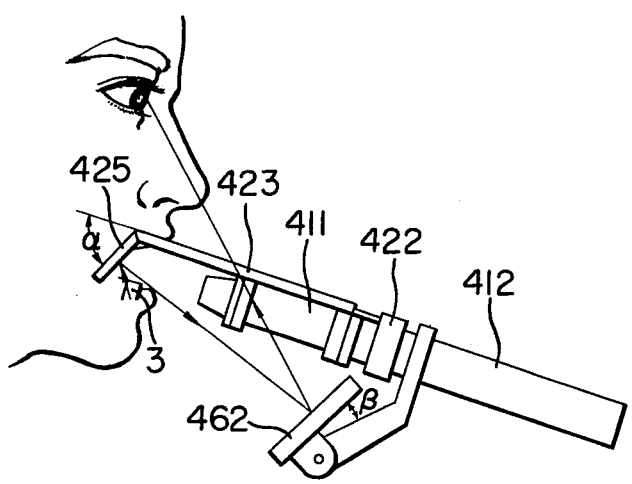

As an alternative way of inspecting the back of a lower fore-tooth, it also will do to inspect by holding the handle 412 so as to locate the ocular mirror 462 beneath the handle and setting the angle of inclination α of the object mirror 425 at about 50°. FIG. 46 illustrated this state.

Figure 43:
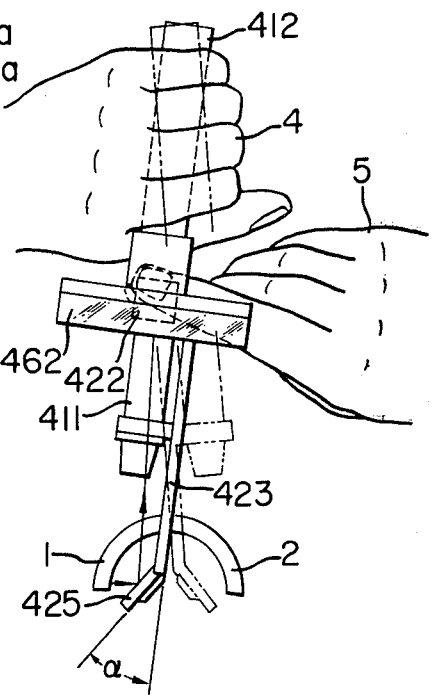
Figure 42:
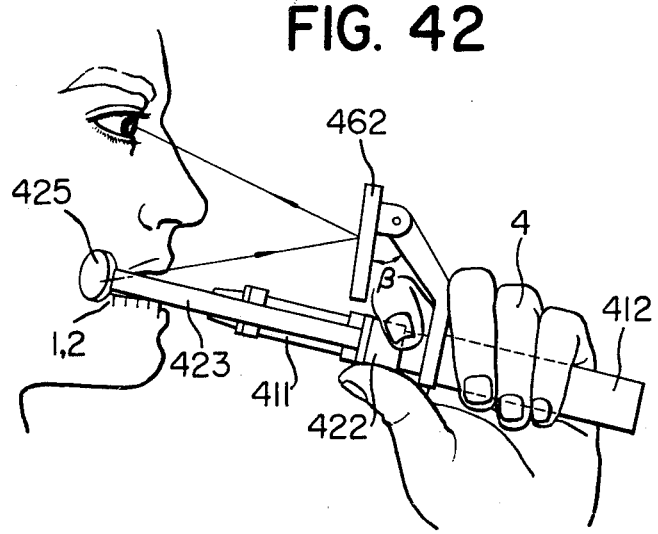

Illustrated in FIGS. 42 and 43 is the state of inspecting the inner side of the lower back-teeth by employing the inspection device of the present invention. FIG. 43 is a plane figure of the state of handling the operating collar 422 by the right hand 5 while holding the handle 412 by the left hand 4. The angle of inclination α of the object mirror 425 is determined by axially moving the operating collar 422 and adjusting it so that the image of a lower back tooth 1 can be thrown back by the object mirror 425 and reflected in the center of the ocular mirror 462; usually, the device is employed in a state such that the angle α be set at the maximum and the collar 422 be raised almost to the full. Next, in order to inspect the inner side of a lower back-tooth 2 on the opposite side, it suffices to turn the operating collar 422 by 180° while leaving the angle α intact and at the same time move the object mirror 425 just a little from the left back-tooth 1 in the direction of the right back-tooth 2.

FIG. 42 is a side view of the state shown in FIG. 43. The hand operating the handle 412 and the operating collar 422 herein represents the state of operating the device by the left hand 4 alone unlike in FIG. 43. The operating collar 422 is operated by the thumb and the forefinger, and the handle 412 is held by the remaining three fingers together with the palm. The angle of inclination β of the ocular mirror 462 is adjusted and determined so that the image can be reflected in the center of the ocular mirror 462 as a state of side-view.

Figure 44:
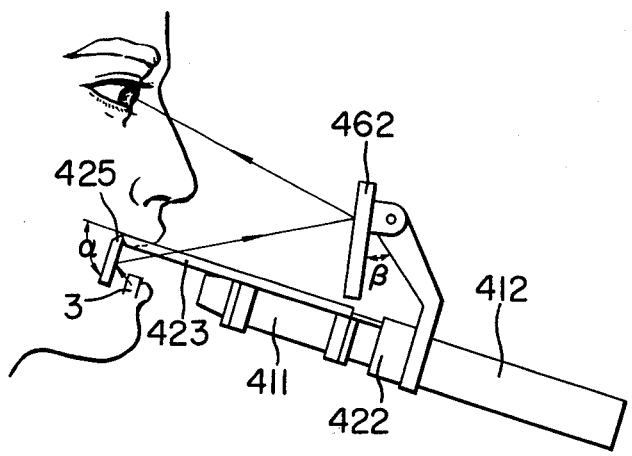
Figure 45:
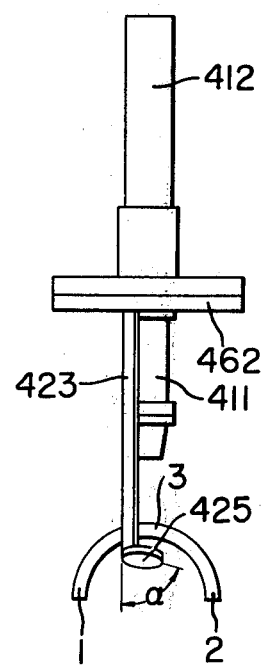

Illustrated in FIGS. 44 and 45 is the state of inspecting the inner side of the lower fore-teeth by employing the inspection device of the present invention. The object mirror 425 is positioned in the inside of the lower fore-teeth 3 by shifting a little from the center as illustrated in the drawing lest the support 423 should obstruct the line of vision (this shifting becomes unnecessary when one is accustomed to operating the device). The operating collar 422 is pulled downward, to wit, to the limit in the direction of the handle, and the object tooth is inspected by setting the angle of inclination α of the object mirror 425 at about the maximum of 90° relative to the support 423.

Figure 2:
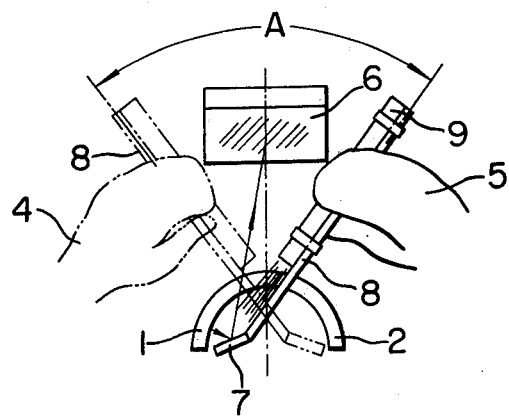
Figure 3:
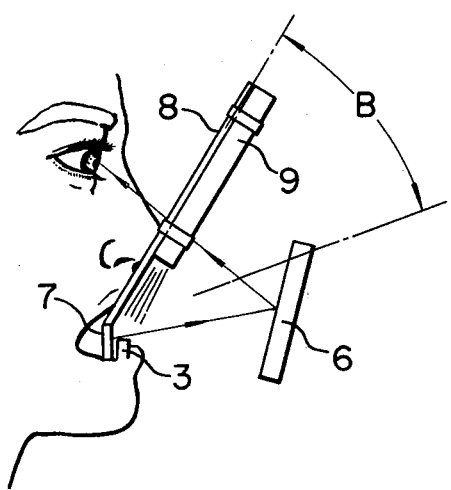
Figure 4:
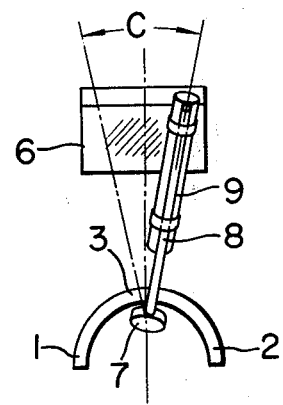
Figure 7:
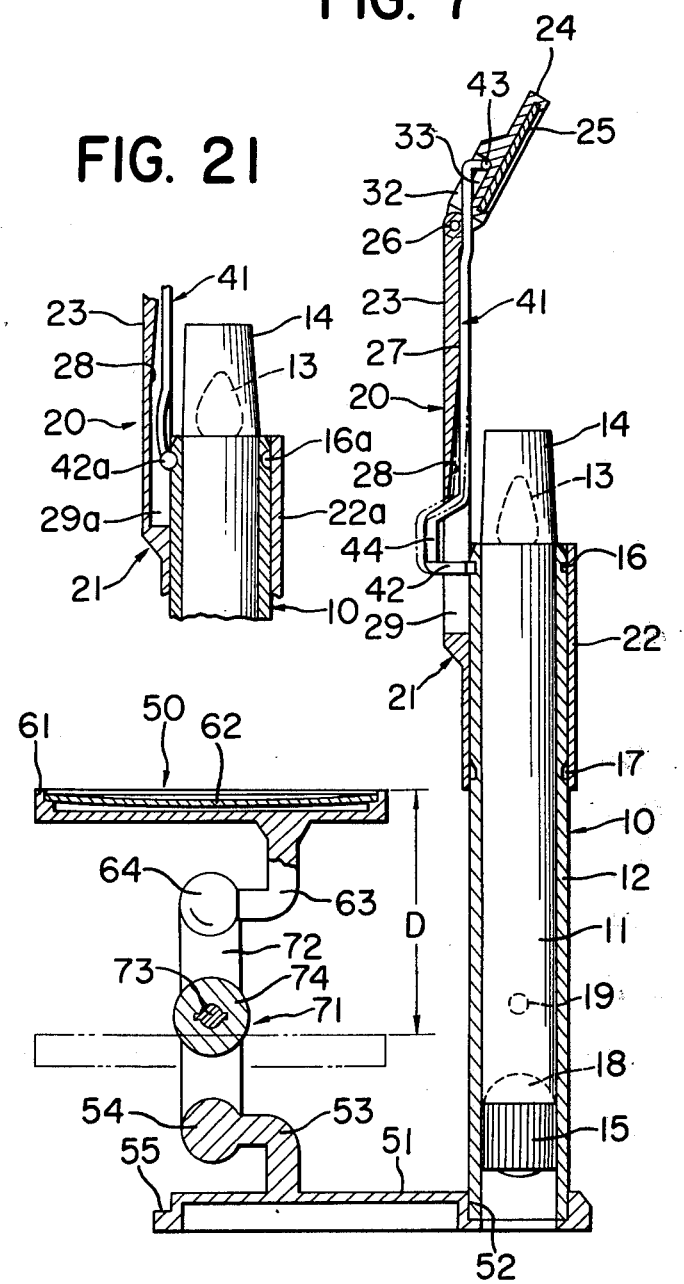
Figure 16:
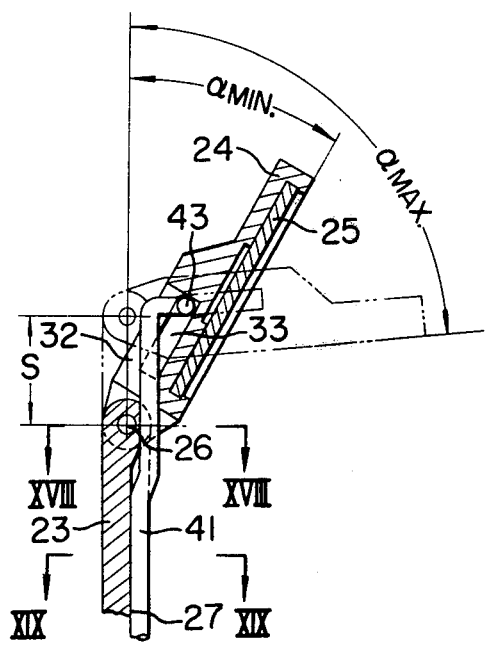
Figure 17:
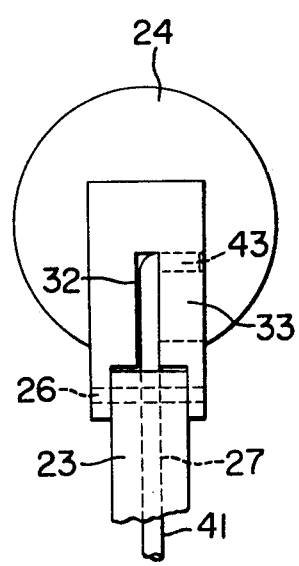
Figure 18:
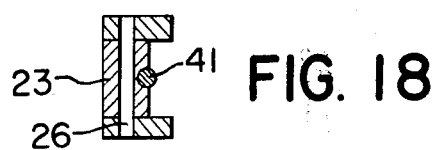
Figure 19:
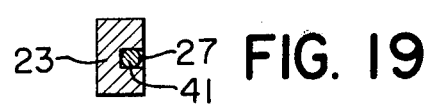

As will be understood from the above descriptions, in inspecting one and the same tooth, in the case of employing a conventional dental mirror 7 such as shown in FIG. 2, the handle 8 must be swung as wide as the horizontal angle A and, accordingly, the way of gripping the handle must be varied and/or the handle must be shifted from the right hand to the left, and vice versa, while in the case of employing an inspection device of the present invention, as illustrated in FIG. 43, it is practically unnecessary to shift the position of the device, and it suffices to rotate the operating collar 422. In the case of employing a conventional dental mirror 7 such as shown in FIG. 3, the handle 8 must be swung as wide as the angle B in vertical direction, while in the case of employing an inspection device of the present invention, as illustrated in FIG. 44, it suffices to lower the operating collar 422 in axial direction, to wit, to move it in the direction of handle 412, and as to the handling of other parts, almost the same as in FIG. 42 applies (that is, it suffices to adjust just slightly the angle of inclination β of the ocular mirror 462).

The foregoing explanation of the way of handling of the inspection devices embodying the present invention in comparison with the conventional device pertains to the inspection of inner side of the lower teeth, but substantially the same applies to the case of other teeth.

In the case of the inspection by the use of a conventional dental mirror 7, what with the collision of the handle 8 with the hand holding the hand-mirror 6 and-/or the hand-mirror 6, it is troublesome and inefficient, and it is difficult to accomplish the object satisfactorily. However, in the case of the inspection device of the present invention, as it is composed by integrating all the components, it is absolutely free from such inconveniences and renders it possible to inspect the object in detail within the range of clear vision.

In the case where it is intended to inspect the outer side of back-teeth by holding a conventional dental mirror by one hand while holding a hand-mirror 6 by the other hand, unless, the corners of the mouth are forced open sideways, the object cannot be seen clearly. Accordingly, one is obliged to place the hand-mirror on a desk or the like and inspect the object by forcing open the mouth by an empty hand while assuming a strained posture with the hand tilted and the back bent. On the contrary, in the case of employing an inspection device of the present invention, inasmuch as the device can be held and operated by one hand, and conduct the inspection in an easy posture by using the other hand for forcing open the mouth.

Although particular preferred embodiments of the invention have been disclosed in detail for illustrative purpose, it will be recognized that variations or modifications of the above disclosed apparatuses, including the arrangement of parts, lie within the scope of the present invention.

What is claimed is:

1. An inspection device, comprising: an elongated body adapted to be grasped by the human hand; an inspection mirror; support structure mounting said inspection mirror on said body, said support structure including a rotatable first support which is rotatable about a first axis of rotation relative to said body and which supports said inspection mirror for arcuate movement as a unit about said first axis of rotation, said first axis of rotation extending lengthwise of said elongated body, said support structure also including a second support which supports said inspection mirror for tilting movement relative to said body about a second axis transverse to said first axis of rotation for changing the inclination of said inspection mirror relative to said body; and actuating means engaged with said inspection mirror for tilting said inspection mirror in response to relative movement between said support structure and said actuating means.

2. An inspection device according to claim 1 in which said rotatable first support is rotatably mounted on said body and said second support is mounted on said first support.

3. An inspection device according to claim 1 wherein said body is equipped with illumination means.

4. An inspection device according to claim 1 wherein said support structure is equipped with illumination means.

5. An inspection device according to claim 1 in which said body has a longitudinally extending cylindrical wall portion, said first support having a sleeve portion at one end thereof which sleeve is rotatably sleeved on said cylindrical wall portion of said body so that said first support is rotatable about the longitudinal axis of said body, said first support extending longitudinally away from said body, said second support comprising a pivot mounted on said first support adjacent the opposite end thereof remote from said body, the axis of said pivot extending substantially perpendicular to said first axis of rotation.

6. An inspection device according to claim 5 in which said sleeve portion of said first support also is axially slidable on said cylindrical wall portion wherein said actuating means is responsive to axial sliding movement of said sleeve portion on said cylindrical wall portion to effect said tilting movement of said inspection mirror.

7. An inspection device according to claim 5 in which said body comprises an elongated hollow cylinder and including illumination means on one end thereof disposed to direct light toward said inspection mirror.

8. An inspection device according to claim 6 wherein said actuating means comprises a rod extending lengthwise along said first support, said first support being axially slidable relative to said rod, one end of said rod being releasably received in an annular circumferential groove in said cylindrical wall portion, the opposite end of said rod being coupled to said inspection mirror for effecting tilting movement of said inspection mirror when said first support is slid axially relative to said rod.

9. An inspection device, comprising: an elongated body adapted to be grasped by the human hand; an inspection mirror; support structure mounting said inspection mirror on said body, said support structure including a rotatable first support which is rotatable about a first axis of rotation relative to said body and which supports said inspection mirror for arcuate movement as a unit about said first axis of rotation, said first axis of rotation extending lengthwise of said elongated body, said support structure also including a second support which supports said inspection mirror for tilting movement relative to said body about a second axis transverse to said first axis of rotation for changing the inclination of said mirror relative to said body; actuating means engaged with said inspection mirror for tilting said inspection mirror in response to relative movement between said support structure and said actuating means; an ocular mirror and means mounting said ocular mirror on said body for receiving images from said inspection mirror.

10. An inspection device according to claim 9 in which said rotatable first support is rotatably mounted on said body and said second support is mounted on said first support.

11. An inspection device according to claim 9 wherein said body is equipped with illumination means.

12. An inspection device according to claim 9 wherein said support structure is equipped with illumination means.

13. An inspection device according to claim 9 wherein said means mounting said ocular mirror includes pivot means so that said ocular mirror can be tilted relative to said body.

14. An inspection device according to claim 9 in which said ocular mirror is a concave mirror.

15. An inspection device according to claim 9 in which said body has a longitudinally extending cylindrical wall portion, said first support having a sleeve portion at one end thereof which sleeve is rotatably sleeved on said cylindrical wall portion of said body so that said first support is rotatable about the longitudinal axis of said body, said first support extending longitudinally away from said body, said second support comprising a pivot mounted on said first support adjacent the opposite end thereof remote from said body, the axis of said pivot extending substantially perpendicular to said first axis of rotation.

16. An inspection device according to claim 15 in which said means mounting said ocular mirror is detachably mounted on said body on the opposite end thereof from said first support.

17. An inspection device according to claim 15 in which said means mounting said ocular mirror comprises a base plate extending laterally from said body for supporting said body in an upright position when said base plate rests on a supporting surface.

18. An inspection device according to claim 17 wherein said ocular mirror is supported on said base plate by a universal joint.

19. An inspection device according to claim 18 wherein said universal joint includes ball joint means.

20. An inspection device according to claim 17 in which said sleeve portion of said first support also is axially slidable on said cylindrical wall portion and wherein said actuating means is responsive to axial sliding movement of said sleeve portion on said cylindrical wall portion to effect said tilting movement of said inspection mirror.

21. An inspection device according to claim 17 in which said body comprises an elongated hollow cylinder and including illumination means on one end thereof disposed to direct light toward said inspection mirror.

22. An inspection device according to claim 20 wherein said actuating means comprises a rod extending lengthwise along said first support, said first support being axially slidable relative to said rod, one end of said rod being releasably received in an annular circumferential groove in said cylindrical wall portion, the opposite end of said rod being coupled to said inspection mirror for effecting tilting movement of said inspection mirror when said first support is slid axially relative to said rod.

23. An inspection device, comprising: an upright elongated cylindrical body which is graspable by the human hand; an upright elongated inspection mirror support extending upwardly from the upper end of said cylindrical body, means mounting said inspection mirror support for rotation about the longitudinal axis of said body; an inspection mirror and means pivotally mounting said inspection mirror on the upper end of said inspection mirror support for pivotal movement about a pivot axis perpendicular to the longitudinal axis of said body for changing the inclination of said inspection mirror relative to said inspection mirror support and said body; and actuating means for pivoting said inspection mirror relative to said inspection mirror support and said body, one of said actuating means and said inspection mirror support being mounted for axially slidable movement relative to said body to pivot said inspection mirror.

24. An inspection device according to claim 23 in which said inspection mirror support is supported for axial sliding movement on said body and said actuating means is a member held against movement relative to said body and connected to said inspection mirror.

25. An inspection device according to claim 23 wherein said actuating means includes a rod whose lower end is releasably fixed to said cylindrical body and whose upper end is engaged with said inspection mirror so that axial sliding movement of said inspection mirror support on said body is effective to pivot said inspection mirror.

26. An inspection device according to claim 23 including illumination means on the upper end of said cylindrical body for directing light toward said inspection mirror, and a switch on said body for operating said illumination means.

27. An inspection device according to claim 23 in which said inspection mirror support is detachably mounted on said cylindrical body.

28. An inspection device according to claim 24 wherein said cylindrical body has a first annular groove therein adjacent the upper end thereof, said actuating means being received in said first groove when the inspection device is in use.

29. An inspection device, comprising: a horizontal base plate adapted to rest on a horizontal support surface; an upright elongated cylindrical body mounted on said base plate and extending upwardly therefrom, said elongated body being graspable by the human hand so that the inspection device can be lifted and moved about; an upright, elongated, inspection mirror support mounted on the upper end of said body and extending upwardly therefrom and means mounting said inspection mirror support for rotation about the longitudinal axis of said body; an inspection mirror and means pivotally mounting said inspection mirror on the upper end of said inspection mirror support for pivotal movement about a pivot axis perpendicular to said longitudinal axis of said body for changing the inclination of said inspection mirror relative to said inspection mirror support and said body; actuating means for pivoting said inspection mirror relative to said inspection mirror support and said body; an ocular mirror support extending upwardly from said base plate at a location thereon sidewardly offset from said cylindrical body, an ocular mirror mounted on the upper end of said ocular mirror support with said ocular mirror being located alongside said body and below and facing upwardly toward said inspection mirror, said ocular mirror support including pivot joint means so that the inclination of said ocular mirror relative to said body can be changed.

30. An inspection device according to claim 29 including an illumination source mounted on the upper end of said cylindrical body for illuminating said inspection mirror.

31. An inspection device, comprising: a horizontal base plate adapted to rest on a horizontal support surface; an upright elongated cylindrical body mounted on said base plate and extending upwardly therefrom, said elongated body being graspable by the human hand so that the inspection device can be lifted and moved about; an upright, elongated, inspection mirror support mounted on the upper end of said body and extending upwardly therefrom and means mounting said inspection mirror support for rotation about the longitudinal axis of said body; an inspection mirror and means pivotally mounting said inspection mirror on the upper end of said inspection mirror support for pivotal movement about a pivot axis perpendicular to said longitudinal axis of said body for changing the inclination of said inspection mirror relative to said inspection mirror support and said body; actuating means for pivoting said inspection mirror relative to said inspection mirror support and said body; an ocular mirror support mounted on said body and extending sidewardly therefrom, an ocular mirror mounted on said ocular mirror support with said ocular mirror being located alongside said body and below and facing upwardly toward said inspection mirror, said ocular mirror support including pivot joint means so that the inclination of said ocular mirror relative to said body can be changed.

32. An inspection device according to claim 31 including an illumination source mounted on the upper end of said cylindrical body for illuminating the inspection mirror.

33. An inspection device according to claim 31 wherein said ocular mirror support is mounted on said body for rotation about the longitudinal axis of said body, and said ocular mirror support includes pivot means supporting said ocular mirror for pivotal movement about a pivot axis perpendicular to the longitudinal axis of said body.

34. An inspection device, comprising: an upright elongated cylindrical body which is graspable by the human hand; an upright elongated inspection mirror support extending upwardly from the upper end of said cylindrical body, means mounting said inspection mirror support for rotation about the longitudinal axis of said body and for axial sliding movement on said body so that the upper end of said inspection mirror support can be moved between a first position adjacent the upper end of said body and a second position remote from the upper end of said body; an inspection mirror and means pivotally mounting said inspection mirror on the upper end of said inspection mirror support for pivotal movement about a pivot axis perpendicular to the longitudinal axis of said body for changing the inclination of said inspection mirror relative to said inspection mirror support and said body; and actuating means for pivoting said inspection mirror relative to said inspection mirror support and said body.

35. An inspection device according to claim 34 in which said actuating means includes means actuated by axial sliding movement of said inspection mirror support on said body.

36. An inspection device according to claim 35 wherein said actuating means includes a rod whose lower end is releasably fixed to said cylindrical body and whose upper end is engaged with said inspection mirror so that axial sliding movement of said inspection mirror support on said body is effective to pivot said inspection mirror.

* * * * *